US006455572B1

(12) United States Patent
Day et al.

(10) Patent No.: US 6,455,572 B1
(45) Date of Patent: Sep. 24, 2002

(54) ESTROGEN AGONIST/ANTAGONIST METABOLITES

(75) Inventors: Wesley W. Day, Old Lyme; Kim A. Johnson, East Haven; Chandra A. Prakash, Gales Ferry; James F. Eggler, Stonington, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/825,980

(22) Filed: Apr. 4, 2001

Related U.S. Application Data

(60) Provisional application No. 60/267,198, filed on Apr. 7, 2000.

(51) Int. Cl.[7] .................... A61K 31/40; A61K 31/4015; C07D 207/26; C07D 207/263; C07D 295/088
(52) U.S. Cl. ................ 514/424; 514/428; 514/567; 548/543; 548/576
(58) Field of Search ............................. 548/543, 576; 562/444; 514/424, 428, 567

(56) References Cited

U.S. PATENT DOCUMENTS

| 3,277,106 A | * 10/1966 | Bencze et al. .............. 548/576 |
| 5,552,412 A | 9/1996 | Cameron et al. ............ 514/317 |
| 5,889,042 A | 3/1999 | MacLeon et al. ............ 514/127 |
| 5,948,809 A | 9/1999 | Chiu et al. .................. 514/428 |
| 6,107,331 A | 8/2000 | MacLean et al. ............ 514/428 |
| 6,153,622 A | 11/2000 | Cameron et al. ............ 514/307 |
| 6,204,286 B1 | 3/2001 | Cameron et al. ............ 514/428 |

FOREIGN PATENT DOCUMENTS

| EP | 0995748 | 4/2000 |

* cited by examiner

*Primary Examiner*—Fiona T. Powers
(74) *Attorney, Agent, or Firm*—Peter C. Richardson; Gregg C. Benson; Todd M. Crissey

(57) ABSTRACT

This invention relates to compounds that are mammalian metabolites of (−)-cis-6-phenyl-5-[4-(2-pyrrolidin-1-yl-ethoxy)-phenyl]-5,6,7,8-tetrahydro-naphthalene-2-ol. The compounds of the invention can be used as standards for analytical assays or as intermediates for the further chemical synthesis or biosynthesis of chemical entities. The invention also relates to pharmaceutical compositions for the treatment of disease and methods of treating disease.

11 Claims, 18 Drawing Sheets

ESTROGEN AGONIST/ANTAGONIST METABOLITES

CROSS REFERENCE TO RELATED APPLICATION

This application claims priority of U.S. provisional application No. 60/267,198, filed Apr. 7, 2000.

FIELD OF THE INVENTION

This invention relates to compounds that are mammalian metabolites of (−)-cis-6-phenyl-5-[4-(2-pyrrolidin-1-yl-ethoxy)-phenyl]-5,6,7,8-tetrahydro-naphthalene-2-ol. The compounds of the invention are useful as standards in analytical assays and as therapeutic agents.

BACKGROUND OF THE INVENTION

Pharmacologically, (−)-cis-6-phenyl-5-[4-(2-pyrrolidin-1-yl-ethoxy)-phenyl]-5,6,7,8-tetrahydro-naphthalene-2-ol (PPTN) is an estrogen agonist/antagonist that is disclosed in U.S. Pat. No. 5,552,412. An "estrogen agonist/antagonist" is compound that affects some of the same receptors that estrogen does, but not necessarily all, and in some instances, it antagonises or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark, et al., *Steroids* 1973;22:707; Capony, et al., *Mol Cell Endocrinol*, 1975;3:233).

The compounds of the present invention are metabolites of PPTN and are believed to possess significant pharmacological activities similar or identical to those possessed by the parent compound; PPTN.

SUMMARY OF THE INVENTION

Figure 1:
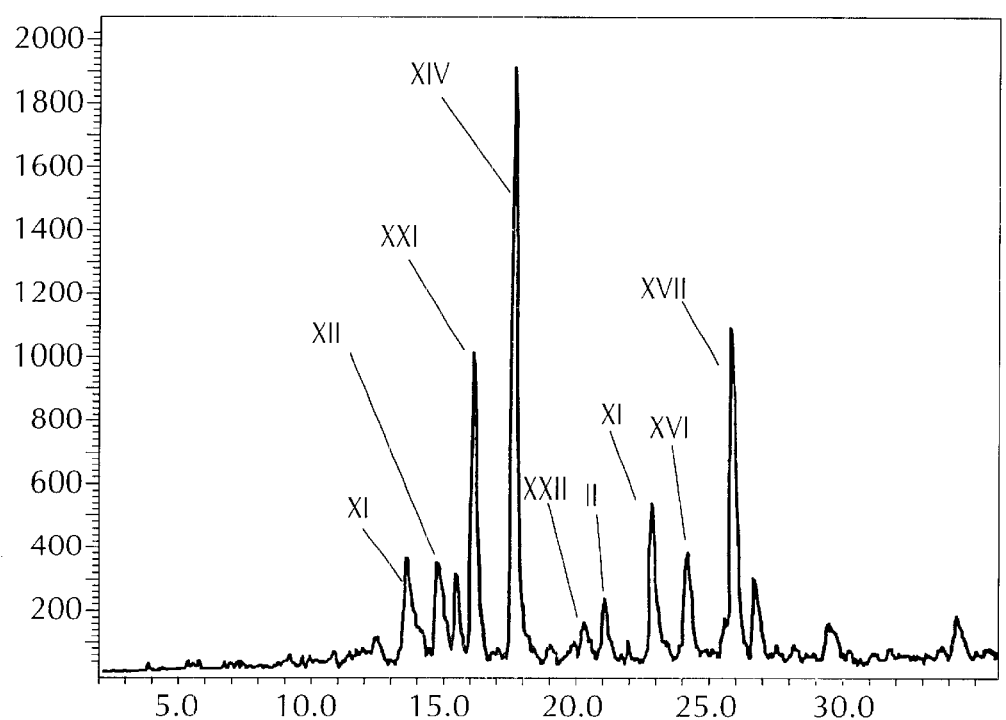
FIG. 1 is a representative HPLC radiochromatogram for urinary metabolites of PPTN in mice following oral administration. The scale of the vertical axis is radioactivity in counts per minute (CPM). The scale of the horizontal axis is retention time in minutes.

This invention relates to compounds that are mammalian metabolites of the estrogen agonist/antagonist; PPTN.

A second aspect of the invention relates to pharmaceutical compositions comprising a metabolite of PPTN or an optical or geometric isomer thereof; or a pharmaceutically acceptable salt, N-oxide, ester, quaternary ammonium salt thereof and a pharmaceutically acceptable carrier, vehicle or diluent.

A third aspect of the invention relates to methods of treating disease comprising administering an effective amount of a metabolite of PPTN possessing pharmacological activity or a pharmaceutically acceptable salt, N-oxide, ester, or quaternary ammonium salt thereof. The metabolites of PPTN are effective while substantially reducing the concomitant liability of adverse effects associated with estrogen administration.

As a fourth aspect, the present invention provides for kits for use by a consumer to treat disease. The kit comprises a) a mammalian metabolite of PPTN; and, optionally, b) instructions describing a method of using the metabolite of PPTN to treat disease. The instructions may also indicate that the kit is for treatment of disease while substantially reducing the concomitant liability of adverse effects associated with estrogen administration.

A fifth aspect of the invention relates to kits for use as analytical standards in measuring metabolites of PPTN or pharmaceutically acceptable salts, N-oxides, esters, and quaternary ammonium salts thereof. The kits comprise a substantially pure form of a PPTN metabolite and a container for holding the metabolite.

As a sixth aspect, the present invention provides for the use of mammalian metabolites of PPTN or pharmaceutically acceptable salts, N-oxides, esters, and quaternary ammonium salts thereof for the manufacture of a medicament.

DETAILED DESCRIPTION OF THE INVENTION

The present invention relates to metabolites of PPTN. The metabolites correspond to compounds represented by Formula I:

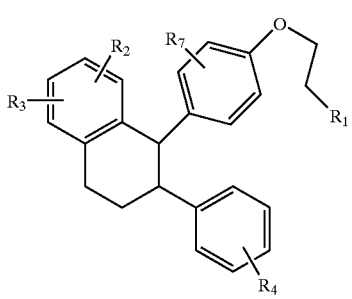
(I)

wherein $R_1$ is selected from

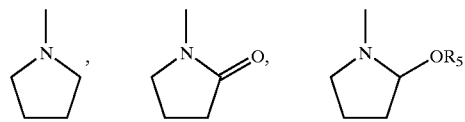

or
—NH(CH$_2$)$_3$COR$_6$;
$R_5$ is selected from H, CH$_3$, glucuronic acid and SO$_3$H;
$R_2$, $R_3$, $R_4$ and $R_7$ are the same or different and are selected from H and OR$_5$; and $R_6$ is selected from —OH, —NHCH$_2$COOH, glucuronic acid and —NHCH$_2$CH$_2$SO$_3$H, provided that:
(a) if $R_1$ is

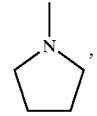

or —NH(CH$_2$)$_3$COOH and
(b) $R_2$ is OH or OCH$_3$ and $R_3$ and $R_7$ are H, or if $R_1$ is as defined in (a) above and
(c) $R_2$ and $R_7$ are H and $R_3$ is OH or OCH$_3$, then $R_4$ is not H.

Preferred compounds of Formula I include compounds wherein:

wherein $R_1$ is selected from

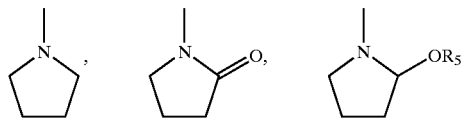

or

—NH(CH$_2$)$_3$COR$_6$;

$R_5$ is selected from H or CH$_3$;

$R_2$, $R_3$, $R_4$ and $R_7$ are the same or different and are selected from H and OR$_5$; and $R_6$ is selected from —OH, or —NHCH$_2$COOH, provided that:
(a) if $R_1$ is

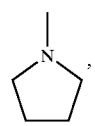

or —NH(CH$_2$)$_3$COOH and
(b) $R_2$ is OH or OCH$_3$ and $R_3$ and $R_7$ are H, or if $R_1$ is as defined in (a) above and
(c) $R_2$ and $R_7$ are H and $R_3$ is OH or OCH$_3$, then $R_4$ is not H.

Preferred metabolite compounds of PPTN include those exemplified in Table I.

TABLE I
Preferred Metabolites of PPTN:
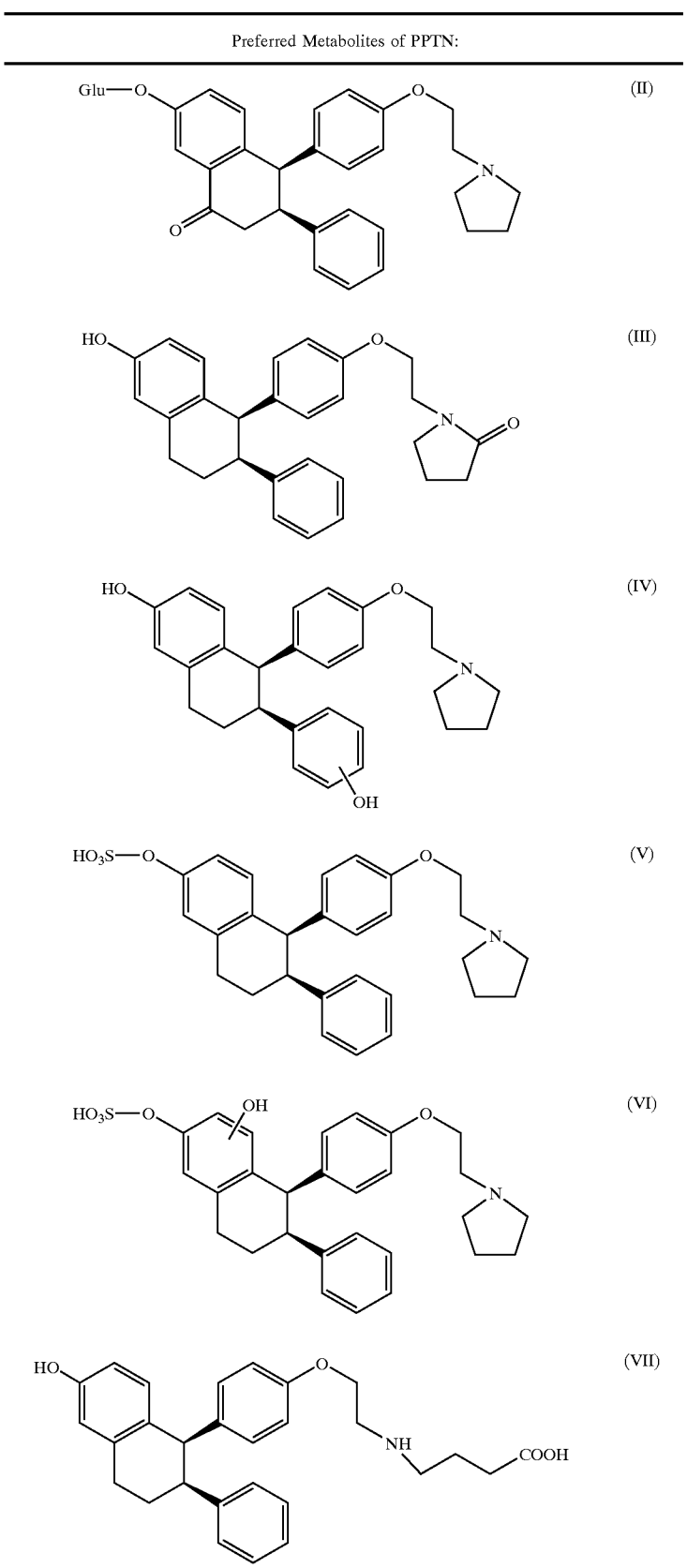

TABLE I-continued
Preferred Metabolites of PPTN:
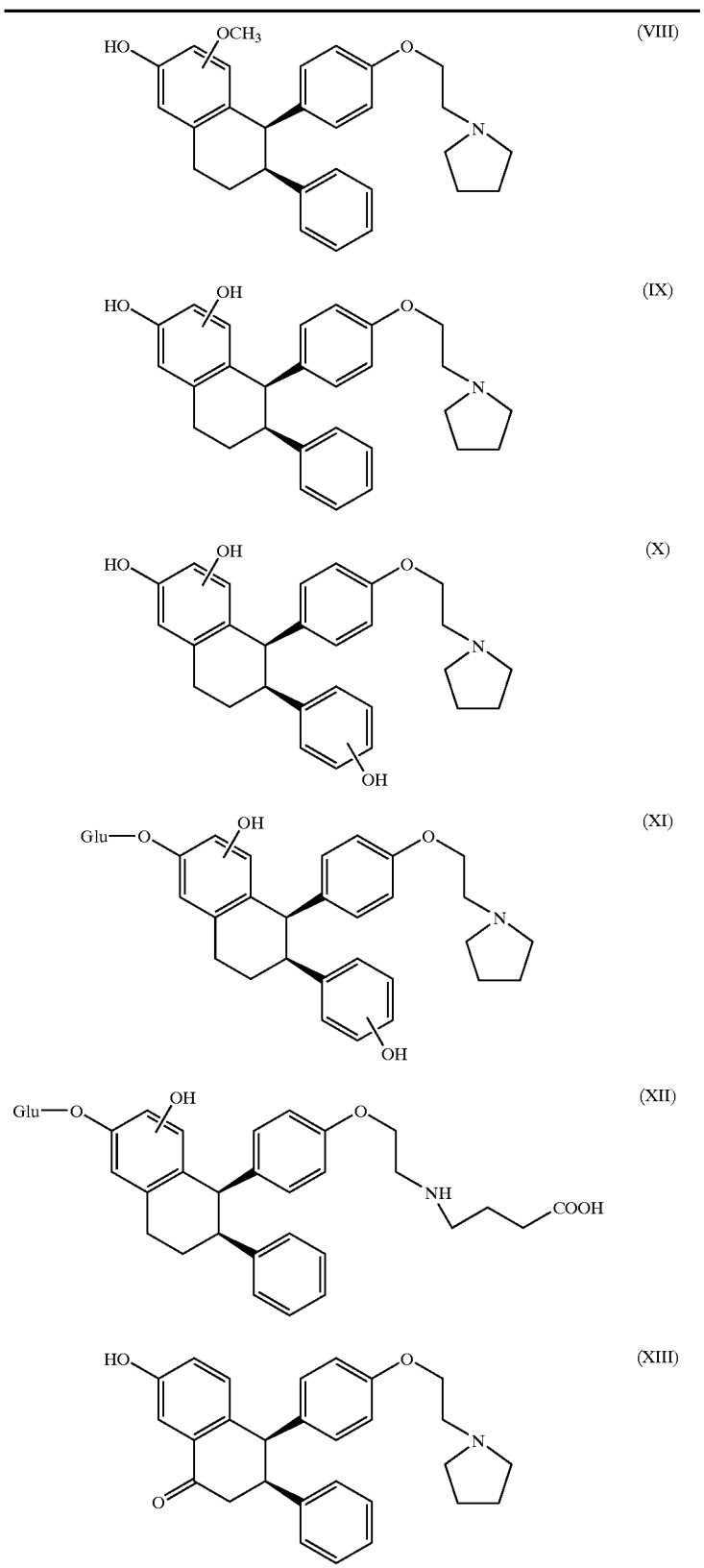

TABLE I-continued
Preferred Metabolites of PPTN:
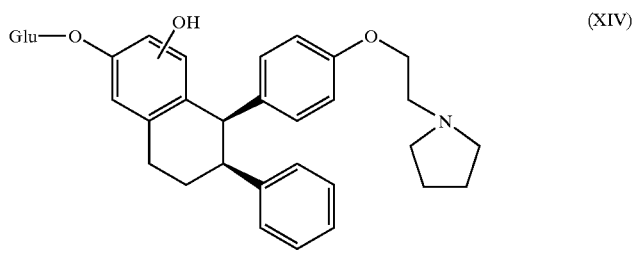 (XIV)
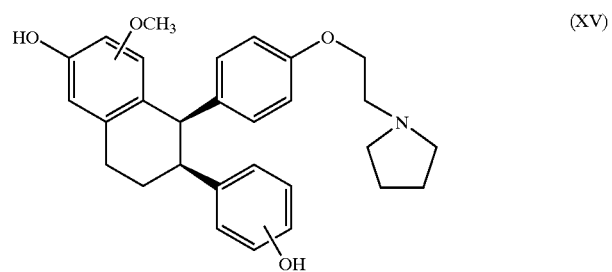 (XV)
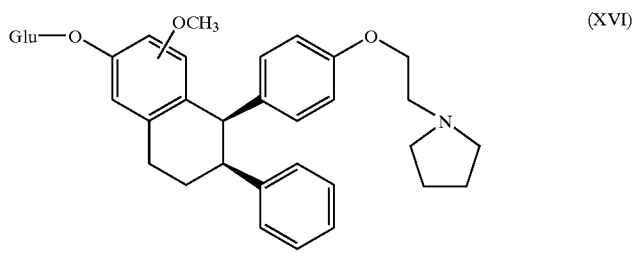 (XVI)
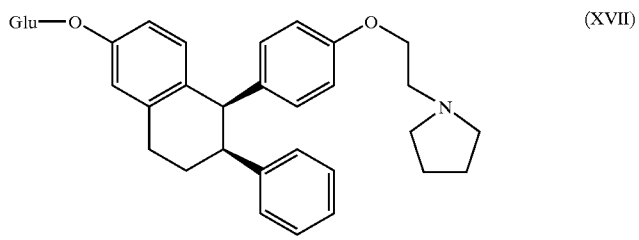 (XVII)
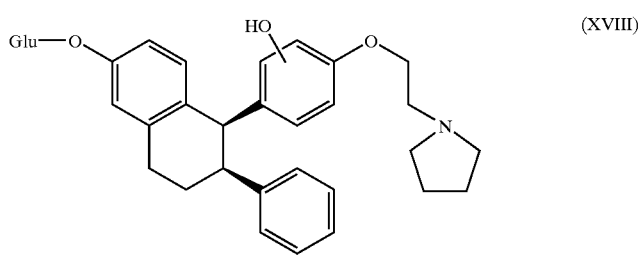 (XVIII)
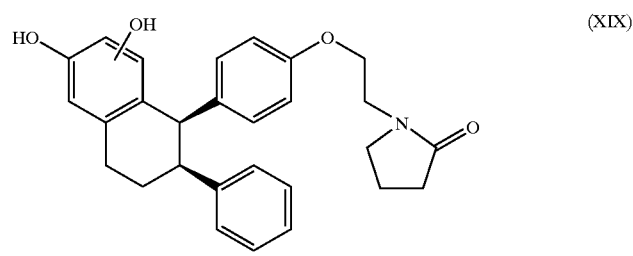 (XIX)

TABLE I-continued
Preferred Metabolites of PPTN:
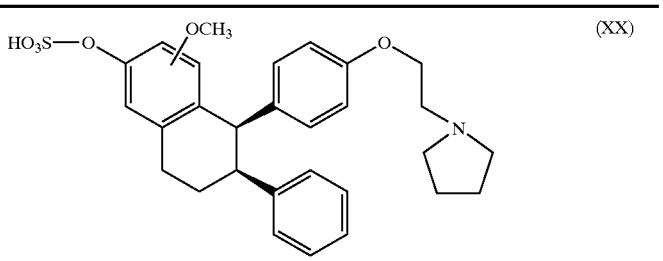 (XX)
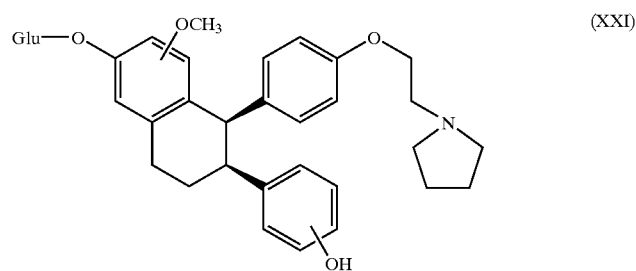 (XXI)
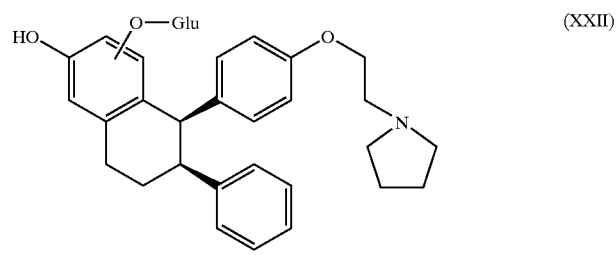 (XXII)
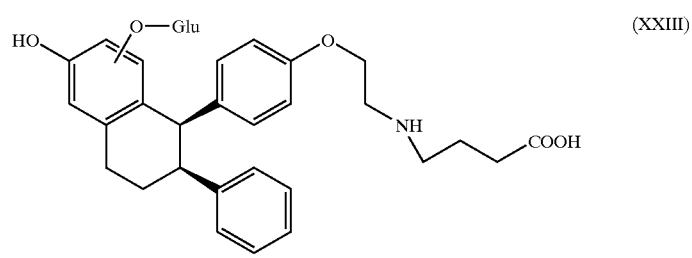 (XXIII)
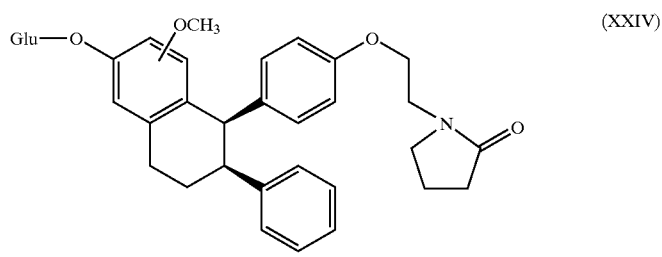 (XXIV)
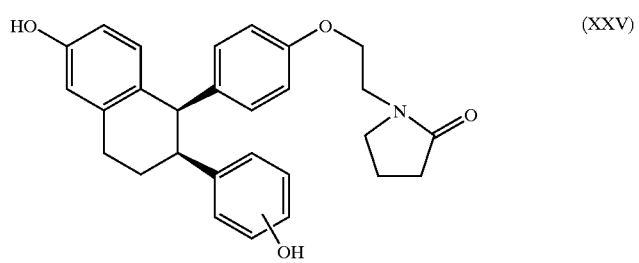 (XXV)

More Preferred metabolite compounds of PPTN include those exemplified in Table II.

TABLE II

Preferred Metabolites of PPTN:

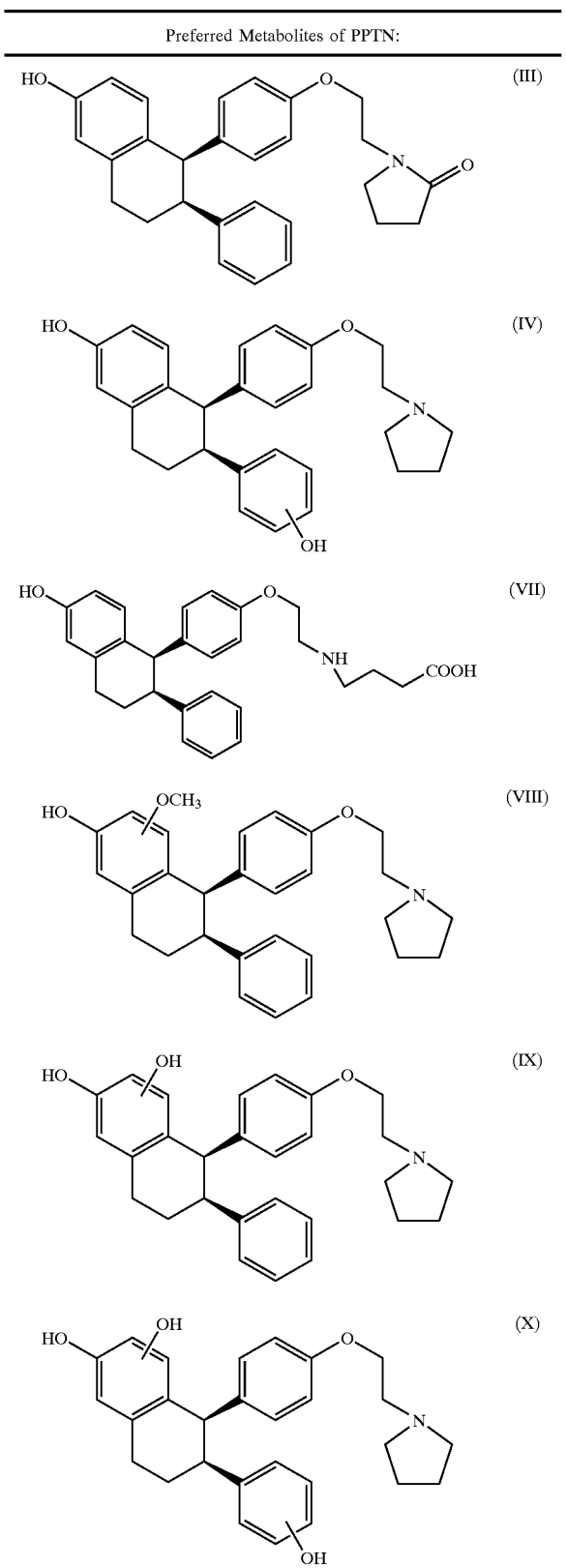

TABLE II-continued

Preferred Metabolites of PPTN:

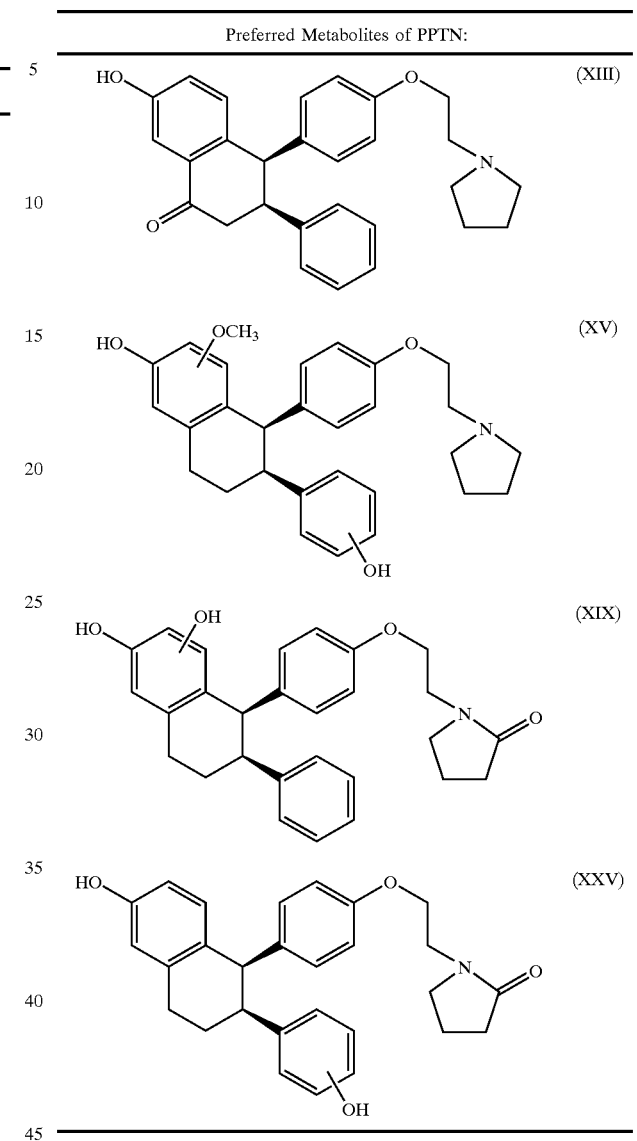

In another aspect, this invention relates to substantially pure metabolites of PPTN as described above.

Unless otherwise stated the following definitions apply:

"Treatment" as used herein includes preventative (e.g., prophylactic) and palliative treatment and "treating" as used herein refers to the act of providing preventative and/or palliative treatment.

A "subject" is an animal including the human species that is treacle with the compounds, compositions, methods and kits of the present invention. The term "subject" or "subjects" is intended to refer to both the male and female gender unless one gender is specifically indicated. Preferred subjects are post-menopausal women.

"Adverse effects associated with estrogen" include breast tenderness, breast cancer, bloating, headache, increased blood clotting and menstrual bleeding in women. Unopposed estrogen therapy increases the risk of endometrial carcinoma. Women on long-term estrogen therapy may have an increased risk that is not reversed by concurrent progestin (*N. Enql. J. Med.* 1995;332:1589). In men, the adverse effects of estrogen include increased blood clotting, gynecomastia, feminization and decreased libido.

The term "post-menopausal women" is defined to include not only women of advanced age who have passed through menopause, but also women who have been hysterectomized or for some other reason have suppressed estrogen production, such as those who have undergone long-term administration of corticosteroids, suffer from Cushions' syndrome or have gonadal dysgenesis.

"Breast cancer" is defined as a malignant proliferation of epithelial cells lining the ducts or lobules of the breast.

"Glucuronic acid" is the substituent that is transferred to a metabolite or transferred to a parent compound to form a metabolite from the phase II conjugation reaction of glucuronidation. Glucuronic acid reacts with an acid or alcohol or phenol moiety on the metabolite or parent compound to form the "glucuronide" The glucoronide substituent is abbreviated in the formulae herein as "Glu" or "Glucuronide".

"Sulfuric acid" is the substituent that is transferred to a metabolite or transferred to a parent compound to form a metabolite from the phase II conjugation reaction of sulfation. Sulfuric acid reacts with an alcohol or phenol moiety on the metabolite or parent compound to form the "sulfate".

"Co-administration" of a combination of a PPTN metabolite and an additional compound or additional compounds means that these components can be administered together as a composition or as part of the same, unitary dosage form. "Co-administration" also includes administering a PPTN metabolite and an additional compound or additional compounds separately but as part of the same therapeutic treatment program or regimen. The components need not necessarily be administered at essentially the same time, although they can if so desired. Thus "co-administration" includes, for example, administering a PPTN metabolite and an additional compound as separate dosages or dosage forms, but at the same time. "Co-administration" also includes separate administration at different times and in any order. For example, where appropriate a patient may take one or more component(s) of the treatment in the morning and the one or more of the other component(s) at night.

The chemist of ordinary skill will recognize that certain compounds of this invention will contain one or more atoms which may be in a particular stereochemical, tautomeric, or geometric configuration, giving rise to stereoisomers, tautomers, regio and configurational isomers. All such isomers and mixtures thereof are included in this invention. Hydrates and solvates of the compounds of this invention are also included.

The subject invention also includes isotopically-labeled compounds, which are identical to those shown in Formulae I-XXV, among other compounds encompassed by the invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$ $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formulae I-XXV of this invention and prodrugs thereof can generally be prepared by carrying out the procedures exemplified below or those known in the art. $^{14}C$-PPTN can be prepared by the methods outlined and exemplified in U.S. Pat. No. 5,552,412 by substituting a readily available isotopically labeled reagent for a non-isotopically labeled reagent.

The metabolites of PPTN, in their substantially pure form or in mixtures of known composition, may be used as analytical standards for in vitro or in vivo metabolism studies or as intermediates for the chemical synthesis or biosynthesis of new chemical entities. The metabolites may be isolated as solids or in solutions.

The compounds of the present invention are believed to be useful for the treatment of disease. Examples of diseases or conditions for which the compounds can be effective include osteoporosis, breast cancer, hyperlipidemia, atherosclerosis, Alzheimer's disease, cataracts, loss of libido, male sexual dysfunction, colon cancer, skin wrinkles, autoimmune disease, alopecia, acne, cardiovascular disease, cataracts, diabetes, endometriosis, female sexual dysfunction, hyperglycemia, obesity, obsessive compulsive disorder, premenstrual syndrome, prostatic carcinoma, benign prostatic hyperplasia, pulmonary hypertension, reperfusion damage, rheumatoid arthritis, osteoarthritis, seborrhea, senile gynecomastia, testosterone deficiency and conditions responsive to testosterone elevation, Turner's syndrome, uterine fibrosis, atrophic vaginitis, incontinence, uterine cancer, hirsutism, bulimia, anorexia, hypoactive sexual desire, sexual arousal disorder, dyspareunia, vagismus, and the promotion of wound healing. The compounds may also be effective in increasing the frequency of orgasm, treating prolapse, lowering vaginal pH, treating urinary tract infections, treating or preventing stroke, myocardial infarction, acute or chronic renal failure, peripheral arterial occlusive disease, and Raynaud's Phenomenon, and treating cancers of the ovary, liver, and pancreas, as well as desmoid cancer, glioma, and renal cell carcinoma. Methods for treating one or more of the above diseases or conditions comprise the administration of an effective amount of a PPTN metabolite.

In the methods of treatment of the present invention, a metabolite can be administered to a subject directly, such as in a table, or the metabolite can be administered by being produced in the subject's body through metabolism. For example, a metabolite of the present invention can be effectively administered to a subject to treat a disease or condition by administering to the subject an amount of PPTN, after which administration, the desired metabolite is formed in the subject's body through metabolism. Moreover, the administration route and dosage of PPTN can be varied, as desired, to obtain desired in vivo concentrations and rates of production of a metabolite.

When used for the treatment of one or more of the above conditions, PPTN metabolites may be used (either co-administered separately or within the same pharmaceutical composition) in combination with PPTN and statins, such as simvastatin, disclosed in U.S. Pat. No. 4,444,784; pravastatin, disclosed in U.S. Pat. No. 4,346,227; cerivastatin, disclosed in U.S. Pat. No. 5,502,199; mevastatin, disclosed in U.S. Pat. No. 3,983,140; velostatin, disclosed in U.S. Pat. No. 4,448,784 and U.S. Pat. No. 4,450,171; fluvastatin, disclosed in U.S. Pat. No. 4,739,073; compactin, disclosed in U.S. Pat. No. 4,804,770; lovastatin, disclosed in U.S. Pat. No. 4,231,938; dalvastatin, disclosed in European Patent Application Publication No. 738510 A2; fluindostatin, disclosed in European Patent Application Publication No. 363934 A1; atorvastatin, disclosed in U.S. Pat. No. 4,681,893; atorvastatin calcium, disclosed in U.S. Pat. No. 5,273,995; dihydrocompactin, disclosed in U.S. Pat. No. 4,450,171; ZD-4522, disclosed in U.S. Pat. No. 5,260,440; bervastatin, disclosed in U.S. Pat. No. 5,082,859; and NK-104, disclosed in U.S. Pat. No. 5,102,888. PPTN metabolites may also be used in combination with bisphosphonate compounds such as alendronic acid, alendronate, cimadronate, clodronic acid, clodronate, 1-hydroxy-3-(1-pyrrolidinyl)-propylidene-1,1-bisphosphonic acid, etidronic acid, ibandronate, neridronate, olpadronate, pamidronate, piridronate, risedronate, tiludronate and zolendronate. Additionally, PPTN metabolites may be used in combination with cyclic guanosine 3',5' monophosphate elevators such as sildenafil (1-[[3-(6,7-dihydro-1-methyl-7-oxo-3-propyl-1H-pyrazolo[4,3-d]pyrimidin-5-yl)-4-ethoxy-phenyl]sufonyl]-4-methylpiperazine citrate salt).

The pharmaceutically acceptable acid addition salts of the compounds of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid.

The compounds of this invention, as discussed above, can be administered in the form of pharmaceutically acceptable salts. The salts are conveniently formed, as is usual in organic chemistry, by reacting a compound of this invention, when basic, with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if a compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

When used as a medicament, the dose of a compound of this invention to be administered to a human is rather widely variable and subject to the judgement of the attending physician. It should be noted that it may be necessary to adjust the dose of a compound when it is administered in the form of a salt, such as a laureate, the salt forming moiety of which has an appreciable molecular weight. The general range of effective administration rates of the compounds is from about 0.001 mg/day to about 200 mg/day. A preferred range is from about 0.01 mg/day to 100 mg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds may be absorbed from the alimentary tract, however, the compounds may be administered percutaneously, or as suppositories for absorption by the rectum, if desired in a given instance. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

In general, all of the compositions are prepared according to methods usual in pharmaceutical chemistry and/or isolated from in vivo or in vitro metabolism reactions such as those exemplified herein. The parent compound, PPTN, is prepared by those procedures outlined and/or exemplified in U.S. Pat. No. 5,552,412. The metabolites may be synthesized directly or may be formed by in vitro or in vivo enzymatic or metabolic reactions such as those described in the Examples.

Methods of formulation are well known in the art and are disclosed, for example, in *Remington: The Science and Practice of Pharmacy*, Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The term "prodrug" means compounds that are transformed in vivo to yield a compound of the present invention. The transformation may occur by various mechanisms, such as through hydrolysis in blood. A good discussion of the use of prodrugs is provided by T. Higuchi and W. Stella, "Pro-drugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1-(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N-($C_1$–$C_6$)alkoxycarbonylaminomethyl, succinoyl, ($_1$C–$C_6$) alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$–$C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^x$-carbonyl, $R^xO$-carbonyl, $NR^xR^{x'}$-carbonyl where $R^x$ and $R^{x'}$ are each independently (($C_1$–$C_{10}$)alkyl, ($C_3$–$C_7$)cycloalkyl, benzyl, or $R^x$-carbonyl is a natural α-aminoacyl or natural α-aminoacyl-natural α-aminoacyl, —$C(OH)C(O)OY^x$ wherein ($Y^x$ is H, ($C_1$–$C_6$)alkyl or benzyl), —$C(OY^{x0})Y^{x1}$ wherein $Y^{x0}$ is ($C_1$–$C_4$) alkyl and $Y^{x1}$ is (($C_1$–$C_6$)alkyl, carboxy($C_1$–$C_6$)alkyl, amino($C_1$–$C_4$) alkyl or mono-N- or di-N,N-($C_1$–$C_6$)alkylaminoalkyl, —$C(Y^{x2})$ $Y^{x3}$ wherein $Y^{x2}$ is H or methyl and $Y^{x3}$ is mono-N- or di-N,N-($C_1$–$C_6$)alkylamino, morpholino, piperidin-1-yl or pyrrolidin-1-yl.

As used herein, the term "effective amount" means an amount of compound of the methods of the present invention that is capable of treating the specific diseases and pathological conditions. The specific dose of a compound administered according to this invention will, of course, be determined by the particular circumstances surrounding the case including, for example, the compound administered, the route of administration, the state of being of the subject, and the severity of the pathological condition being treated.

Advantageously, the present invention also provides kits for use by a consumer for treating disease. The kits comprise a) a pharmaceutical composition comprising an estrogen agonist/antagonist and a pharmaceutically acceptable carrier, vehicle or diluent; and, optionally, b) instructions describing a method of using the pharmaceutical composition for treating the specific disease. The instructions may also indicate that the kit is for treating disease while substantially reducing the concomitant liability of adverse effects associated with estrogen administration.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc . . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Based on a reading of the present description and claims, certain modifications to the compositions and methods described herein will be apparent to one of ordinary skill in the art. The claims appended hereto are intended to encompass these modifications.

All references and patents cited herein are incorporated by reference.

EXAMPLES

The following abbreviations are used herein.

| HOAc | acetic acid |
|---|---|
| Ph | phenyl |
| BuLi | n-butyl lithium |
| Et$_2$O | diethyl ether |
| NBS | n-bromosuccinamide |
| DMF | dimethylformamide |
| AIBN | azodiisobutyronitrile |
| Me | methyl |
| EtOH | ethanol |
| rt | room temperature |
| THN | tetrahydronaphthalene |

Example 1

Estrogen Receptor Binding

Estrogen and PPTN metabolite binding affinity is measured by the following protocol:

cDNA cloning of human ERα: The coding region of human ERα is cloned by RT-PCR from human breast cancer cell mRNA using Expand™ High Fidelity PCR System according to manufacturer's instructions (Boehringer-Mannheim, Indianapolis, Ind.). PCR products are cloned into pCR2.1 TA Cloning Kit (Invitrogen, Carlsbad, Calif.) and sequenced. Each receptor coding region is subcloned into the mammalian expression vector pcDNA3 ((Invitrogen, Carlsbad, Calif.).

Mammalian cell expression. Receptor proteins are overexpressed in 293T cells. These cells, derived from HEK293 cells (ATCC, Manassas, Va.), have been engineered to stably express large T antigen and can therefore replicate plasmids containing a SV40 origin of replication to high copy numbers. 293T cells are transfected with either hERα-pcDNA3 or hERβ-pcDNA3 using lipofectamine as described by the manufacturer (Gibco/BRL, Bethesda, Md.). Cells are harvested in phosphate buffered saline (PBS) with 0.5 mM EDTA at 48 h post-transfection. Cell pellets are washed once with PBS/EDTA. Whole cell lysates are prepared by homogenization in TEG buffer (50 mM Tris pH 7.4, 1.5 mM EDTA, 50 mM NaCl, 10% glycerol, 5 mM DTT, 5 µg/ml aprotinin, 10 µg/ml leupeptin, 0.1 mg/ml Pefabloc™ (Pentapharm AG, Basel, Switzerland) using a dounce homogenizer. Extracts are centrifuged at 100,000×g for 2 h at 4° C. and supernatants are collected. Total protein concentrations are determined using BioRad reagent (BioRad, Hercules, Calif.).

Competition binding assay. The ability of PPTN metabolites to inhibit [$^3$H]-estradiol binding is measured by a competition binding assay using dextran-coated charcoal as has been described (Leake R E, Habib F 1987 Steroid hormone receptors: assay and characterization. In: B. Green and R. E. Leake (eds). Steroid Hormones a Practical Approach. IRL Press Ltd, Oxford. 67-92.) 293T cell extracts expressing either hERα or hERβ are incubated in the presence of increasing concentrations of PPTN metabolite and a fixed concentration of [$^3$H]-estradiol (141 µCi/mmol, New England Nuclear, Boston, Mass.) in 50 mM TrisHCl pH 7.4, 1.5 mM EDTA, 50 mM NaCl, 10% glycerol, 5 mM DTT, 0.5 mg/mL β-lactoglobulin in a final volume of 0.2 mL. All PPTN metabolites are dissolved in dimethylsulfoxide or aqueous solvent. The final concentration of receptor is 50 pM with 0.5 nM [3H]-estradiol. After 16 h at 4° C., dextran-coated charcoal (20 µL) is added. After 15 min at room temperature the charcoal is removed by centrifugation and the radioactive ligand present in the supernatant is measured by scintillation counting. All reagents are obtained from Sigma (St. Louis, Mo.) unless otherwise indicated.

Example 2

Inhibition of In Vitro Human Breast Tumor Cell Growth

The in vitro antiproliferative effects of PPTN metabolites are tested using two types of human breast cancer cell lines: first, MCF-7 cells, which contain ER as well as progesterone receptors (PgR), and second, MDA-MB-231 cells, which lack ER and PgR, and enable the determination of an effect that is independent of the ER mechanism. The effect of PPTN metabolites on the growth of these different cell lines is determined by incubation of the cells with various estrogen agonist/antagonist concentrations for 6 days. The antiproliferative effects are then determined by direct cell counts.

Example 3

Biosynthesis of PPTN Metabolites in Mice

A dose of $^{14}$C-PPTN is prepared as a suspension in 0.5% methylcellulose (W/W) at a concentration of about 0.898 mg/g. The dosing solution is assayed in duplicate before and after dosing. Metabolites of PPTN are determined by high performance liquid chromatography (HPLC) with radioactivity detection and identified by liquid chromatography with mass spectrometry/mass spectrometry analysis (LC/MS/MS).

For this Example, a group of CD-1 mice (N=9/gender, 25–30 g) is dosed by oral gavage and housed separately in groups of three animals per cage (3/sex) in Nalgene™ metabolism cages (Nalge Nunc International, Rochester, N.Y.) for the separate collection of urine and feces. The gavage tube is weighed before and after dosing to determine the actual dose given to each animal. Urine, feces and cage washes are quantitatively collected into preweighed sample containers for seven days from each cage at 0–24, 24–48, 48–72, 72–96, 96–120, 120–144 and 144–168 hours post dose. The weights of urine, feces and cage rinse obtained at different time points are recorded. The urine and fecal samples are divided and stored at −20° C. in the dark until analysis. A second group of animals (N=6/gender, 25–30 g) is dosed by oral gavage for the identification of circulating metabolites. In this second group, 3 animals of each gender are sacrificed at 1 and 4 hours post dose and blood is collected in heparinized tubes.

Urine (approximately 3 ml from the 0–48 hour pool) from each group is centrifuged and the supernatant is transferred to a clean tube and concentrated under nitrogen with an evaporator. The residue is dissolved in approximately 1 ml of HPLC mobile phase and an aliquot (80–100 μl) is injected onto the HPLC without further purification. The fecal homogenates (~2 g) from the animals at 0–72 hours post dose are pooled on the basis of weights collected at each time interval and the pooled samples are diluted with acetonitrile (6 ml). The suspension is stirred overnight on a magnetic stirrer and centrifuged. The supernatant is removed, and the extraction is repeated with methanol (6 ml) and methanol:water (50:50, 6 ml). All the supernatants are combined and small aliquots are counted. The organic solvent is evaporated using the Turbo Vap. The residue is dissolved in approximately 1 ml of methanol:ammonium acetate (1:1). An aliquot (20–50 μl) is injected onto the HPLC. Pooled plasma (2 ml, 1 and 4 hour) is diluted with 4 ml of acetonitrile and the precipitated protein are removed by centrifugation. The pellet is washed with an additional 2 ml of acetonitrile and both the supernatants are combined. The supernatants are concentrated on an evaporator, and the residues are reconstituted in 500 μl of methanol:ammonium acetate (1:1). An aliquot (100 μl) is injected on the HPLC.

HPLC is carried out with a Hewlett Packard HP1100 quaternary pump and autosampler (Hewlett Packard, Palo Alto, Calif.) equipped with a radioactivity detector (β-RAM, IN/US Systems, Inc., Tampa, Fla.). Chromatography is carried out on a Beckman Ultrasphere™ C-18 column (4.6 mm×250 mm, 5 μm) (Beckman Coulter, Inc., Fullerton, Calif.) with a binary mixture of 10 mM ammonium acetate (solvent A) and methanol (solvent B). The mobile phase initially consists of solvent A/solvent B (80:20), it is then linearly programmed to solvent A/solvent B (20:80) over 30 min and then programmed to solvent A/solvent B (5:95) in 5 minutes and held for 5 min. The mobile phase composition is returned to the starting solvent mixture over 5 min. The system is allowed to equilibrate for approximately 15 min before making the next injection. A flow rate of 1.0 ml/min is used for all analyses.

Quantification of the metabolites is carried out by measuring the radioactivity in the individual peaks that are separated by HPLC using the radioactivity detector. The radioactivity detector provides an integrated printout in counts per minute (CPM) and the percentage of the radiolabelled material, as well as the peak representation. The radioactivity detector is operated in the homogeneous liquid scintillation counting mode with the addition of 3 ml/min of mobile phase-compatible scintillation cocktail to the effluent post-uv detection.

Identification of the metabolites is performed on a Finnigan TSQ 7000 LC/MS/MS (Thermo Quest, San Jose, Calif.). The effluent from the HPLC column is split and about 50 μl/min is introduced into the mass spectrometer atmospheric ionization source via a pneumatically assisted electrospray interface. The remaining effluent is directed into the flow cell of the radioactivity detector. The radioactivity detector response is recorded in real time by the mass spectrometer data system which provides simultaneous detection of radioactivity and mass spectrometry data. The delay in response between the two detectors is about 0.2 min with the mass spectrometric response recorded earlier. The electrospray interface is operated at about 4000 V and the mass spectrometer is operated in the positive mode. Collision induced dissociation (CID) studies are performed using argon gas at a collision energy of about 30 to about 40 eV and a collision gas pressure of about 2.3 mTorr.

Example 4

Biosynthesis of PPTN Metabolites in Humans $^{14}$C-PPTN (tartrate salt) is prepared with a specific activity of about 1.93 mCi/mMol.

Normal healthy male subjects between the ages of 18 and 45 years are chosen to participate in the study. Subjects enter the clinical facility approximately 12 hours before dosing, and remain there for at least 576 hours after dosing under continuous medical observation. All subjects fast for at least 12 hours before being given a single dose of approximately 20 mg free base equivalents of $^{14}$C-PPTN (~80 μCi/subject). The dose is administered in an open fashion in the morning. A standard meal is provided 4 hours later. The dosing formulation is prepared by suspending the radiolabeled PPTN in water. Subjects are required to refrain from lying down, eating or drinking caffeinated and carbonated beverages during the first four hours after rug administration.

After dosing, blood sufficient to yield 20 ml of plasma was collected at 24 and 48 hours for the purposes of metabolite identification. All samples are labeled and immediately frozen.

Plasma samples (20 ml) from each subject at 24 and 48 hours post dose are mixed with 40 ml of acetonitrile, vortexed and sonicated. The mixtures are centrifuged and the supernatants removed. The pellets are mixed with 5 ml of acetonitrile, centrifuged, and the two supernatants are combined. The supernatants are concentrated to dryness under nitrogen. The residues are reconstituted in 300 μl of methanol/water (1:1), centrifuged to remove insoluble matters, and 100 μl aliquots are injected into the HPLC column. PPTN metabolites extracted from the plasma samples are identified by HPLC with radioactivity detection and by LC/MS/MS as described in Example 3 above.

Example 5

Isolation and Identification of Mouse PPTN Metabolites

Figure 2:
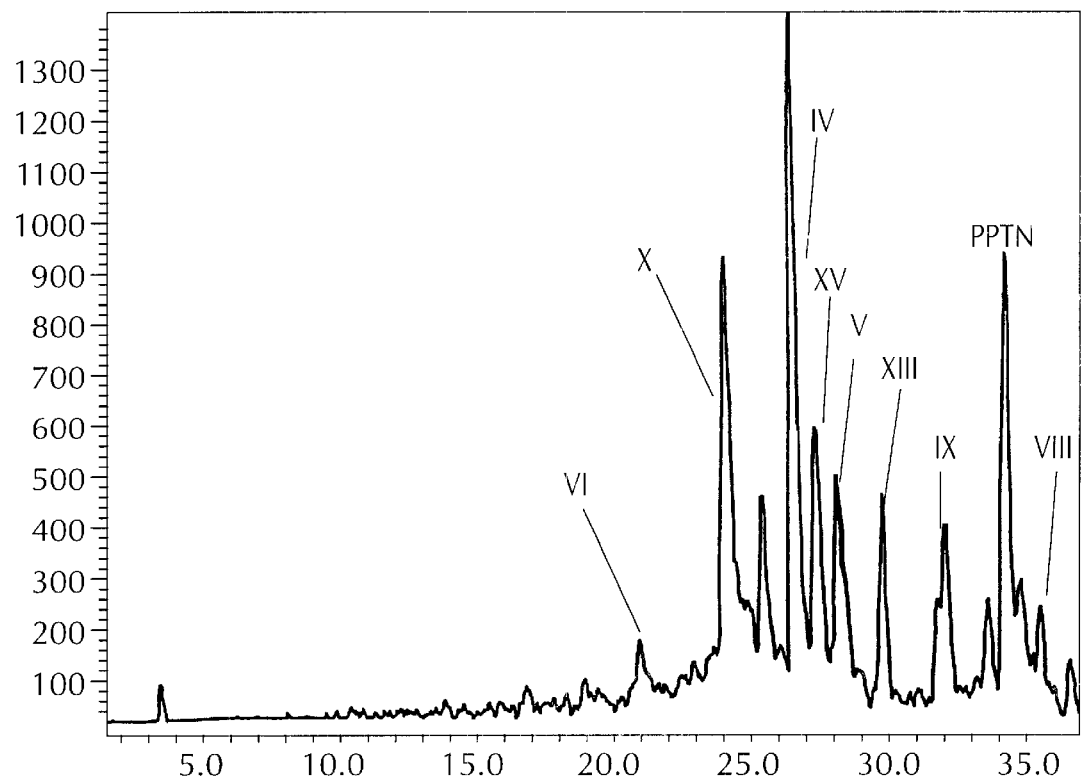
FIG. 2 is a representative HPLC radiochromatogram for fecal metabolites of PPTN in mice following oral administration. The scale of the vertical axis is radioactivity in counts per minute (CPM). The scale of the horizontal axis is retention time in minutes.
Figure 3:
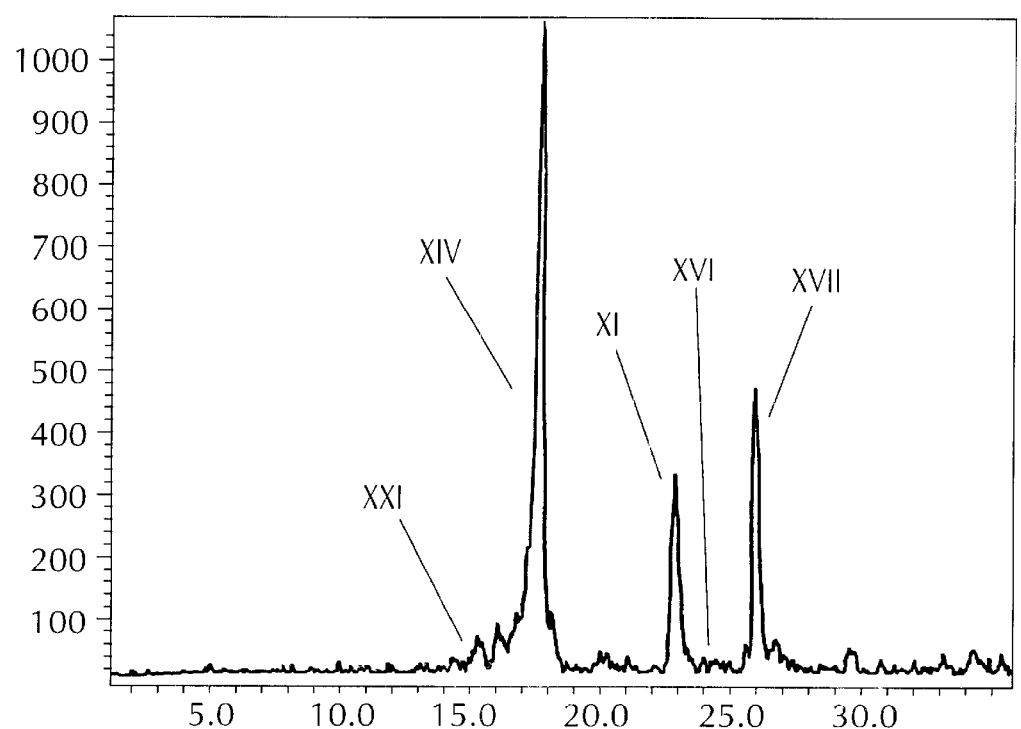
FIG. 3 is a representative HPLC radiochromatogram for circulating metabolites of PPTN in mice following oral administration. The scale of the vertical axis is radioactivity in counts per minute (CPM). The scale of the horizontal axis is retention time in minutes.
Figure 4A:
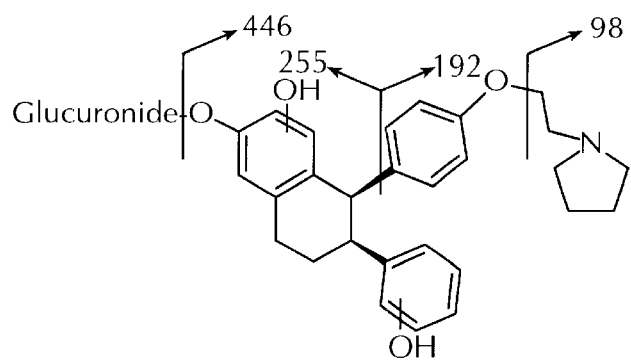
FIG. 4 is the fragmentation pattern and mass spectral data for PPTN metabolite XI. The scale of the vertical axis is relative abundance. The scale of the horizontal axis is the mass to charge ratio; m/z.
Figure 4B:
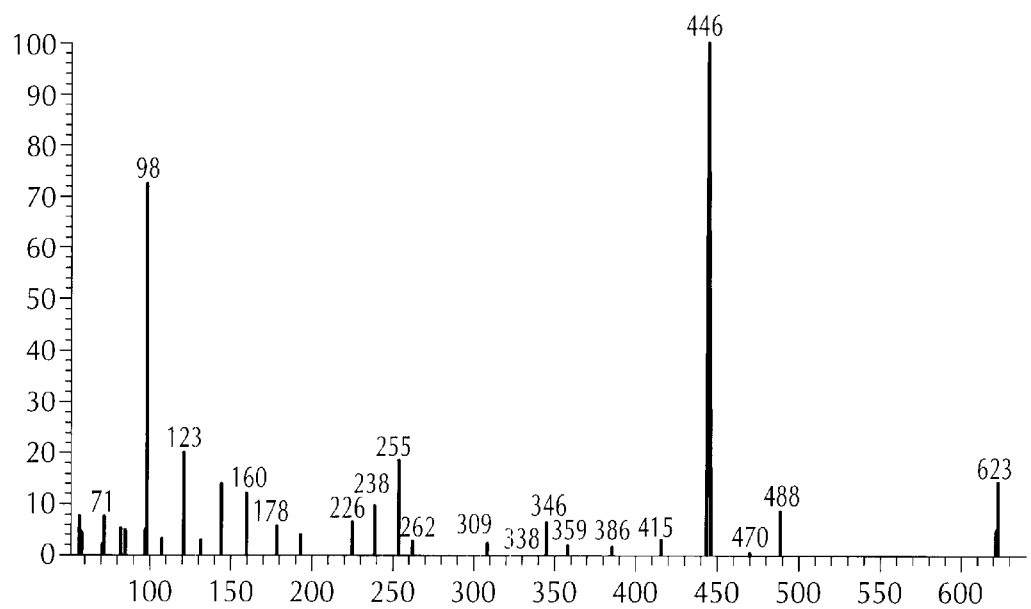
Figure 5A:
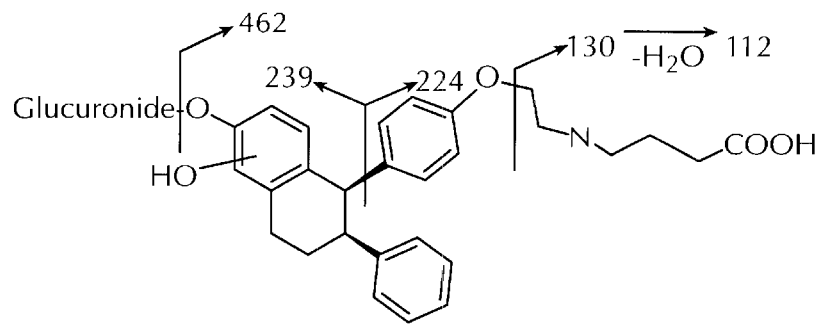
FIG. 5 is the fragmentation pattern and mass spectral data for PPTN metabolite XII. The scale of the vertical axis is relative abundance. The scale of the horizontal axis is the mass to charge ratio; m/z.
Figure 5B:
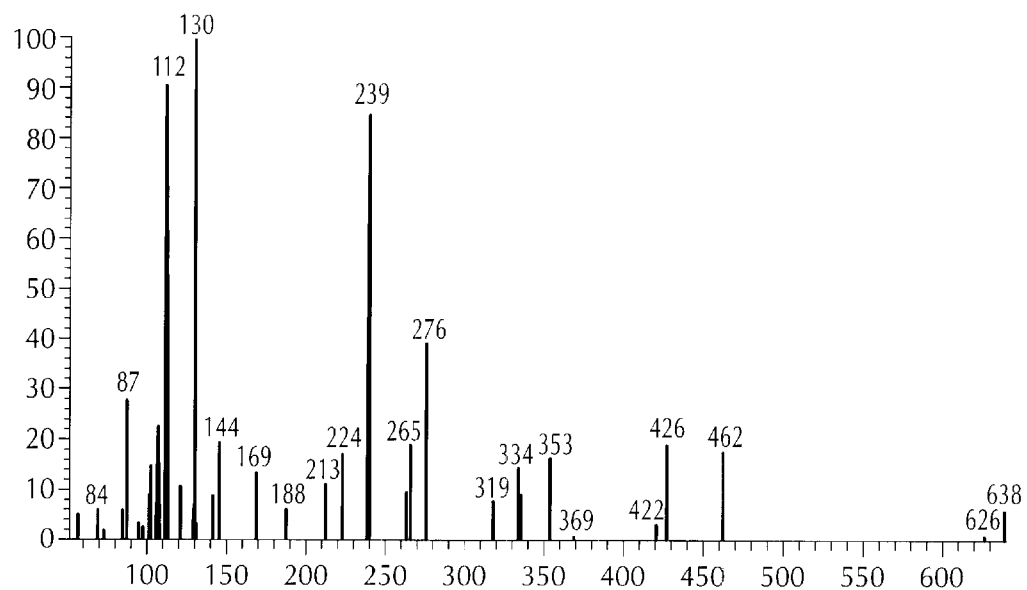
Figure 6A:
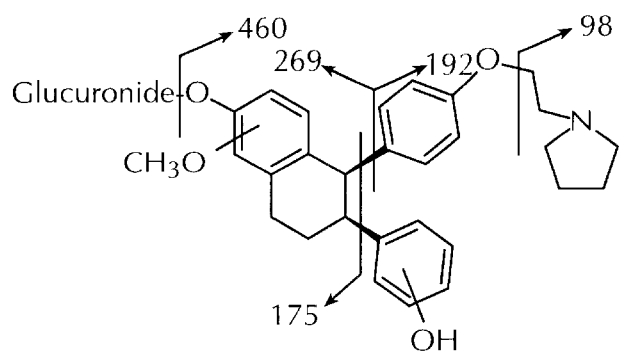
FIG. 6 is the fragmentation pattern and mass spectral data for PPTN metabolite XXI. The scale of the vertical axis is relative abundance. The scale of the horizontal axis is the mass to charge ratio; m/z.
Figure 6B:
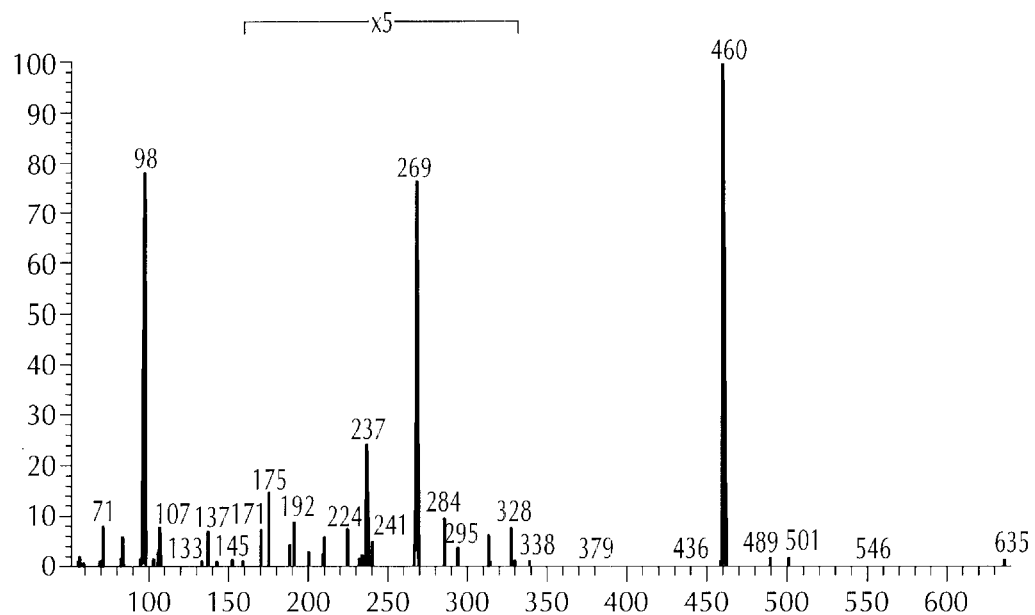
Figure 7A:
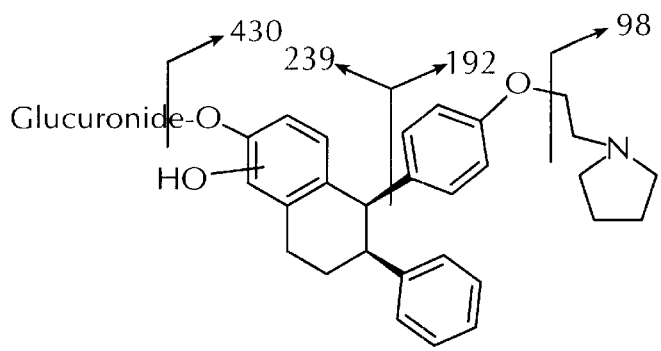
FIG. 7 is the fragmentation pattern and mass spectral data for PPTN metabolite XIV. The scale of the vertical axis is relative abundance. The scale of the horizontal axis is the mass to charge ratio; m/z.
Figure 7B:
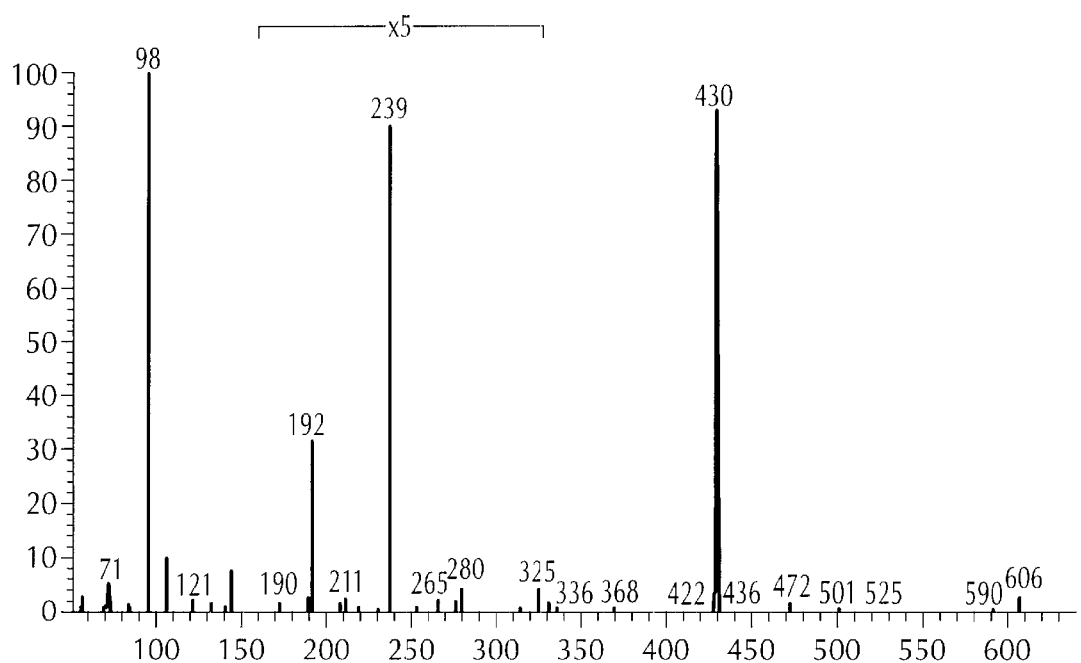
Figure 8A:
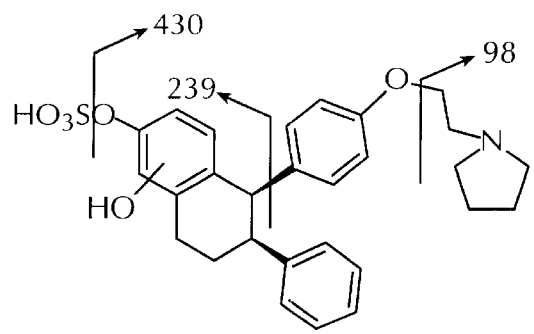
FIG. 8 is the fragmentation pattern and mass spectral data for PPTN metabolite VI. The scale of the vertical axis is relative abundance. The scale of the horizontal axis is the mass to charge ratio; m/z.
Figure 8B:
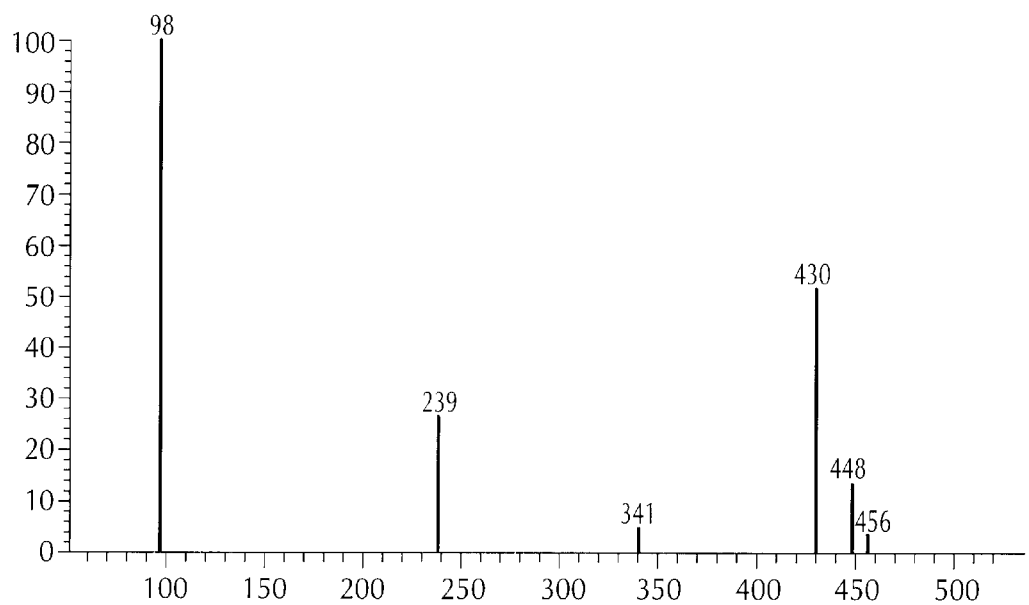
Figure 9A:
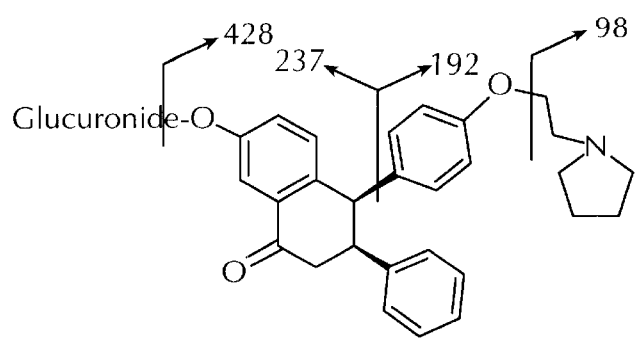
FIG. 9 is the fragmentation pattern and mass spectral data for PPTN metabolite II. The scale of the vertical axis is relative abundance. The scale of the horizontal axis is the mass to charge ratio; m/z.
Figure 9B:
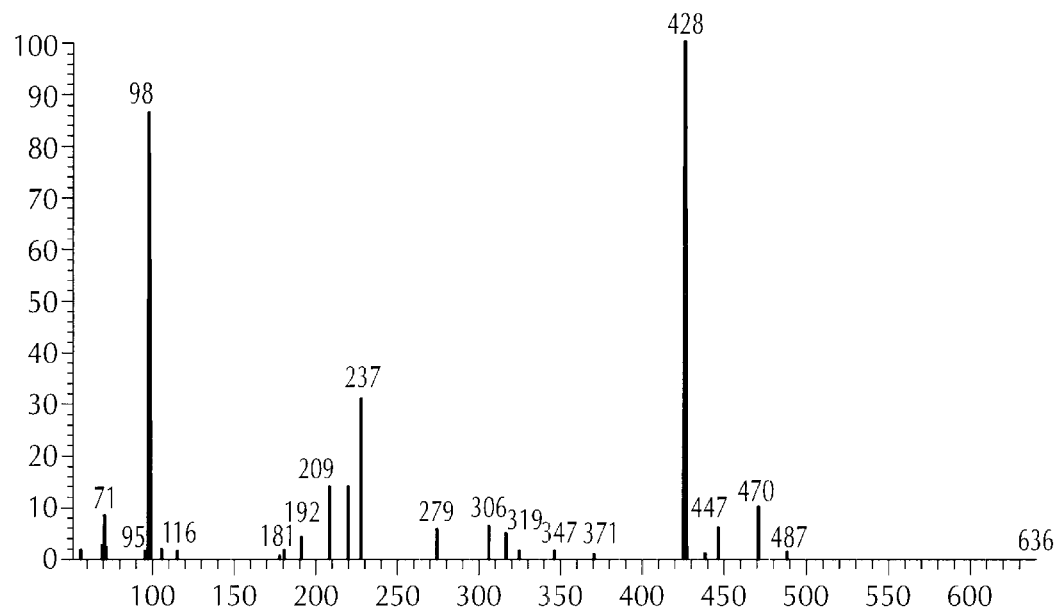
Figure 10A:
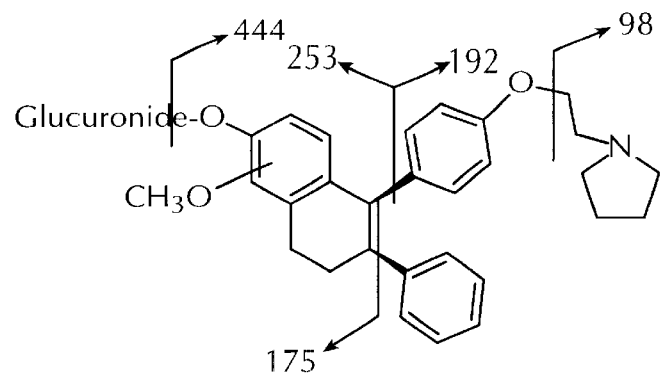
FIG. 10 is the fragmentation pattern and mass spectral data for PPTN metabolite XVI. The scale of the vertical axis is relative abundance. The scale of the horizontal axis is the mass to charge ratio; m/z.
Figure 10B:
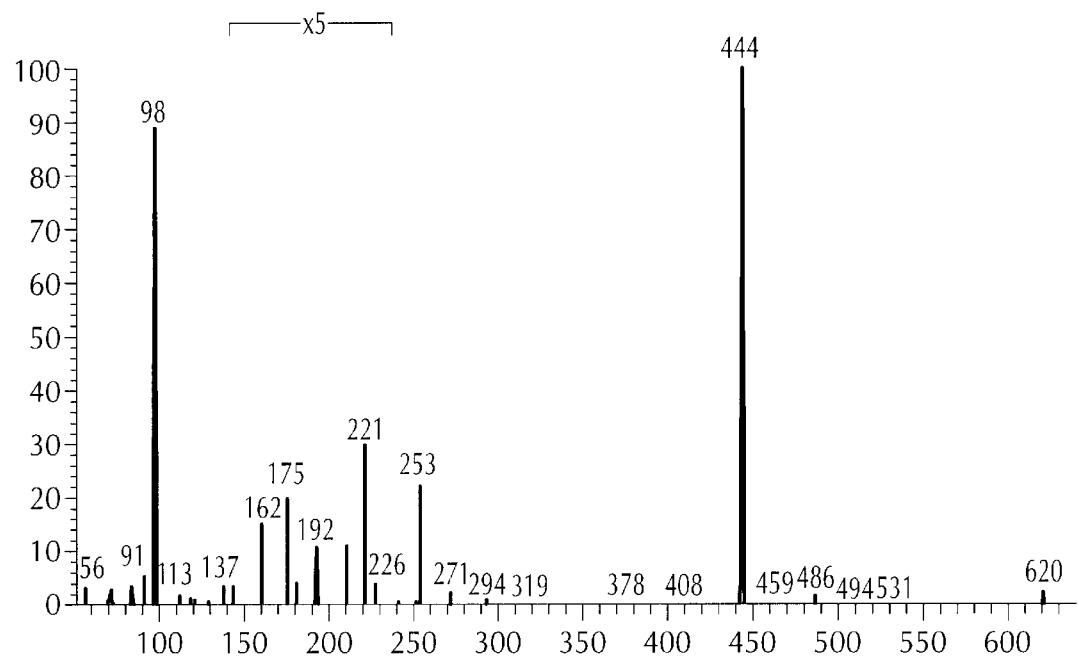
Figure 11A:
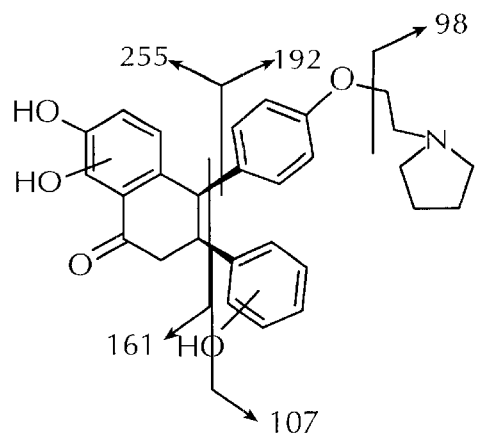
FIG. 11 is the fragmentation pattern and mass spectral data for PPTN metabolite X. The scale of the vertical axis is relative abundance. The scale of the horizontal axis is the mass to charge ratio; m/z.
Figure 11B:
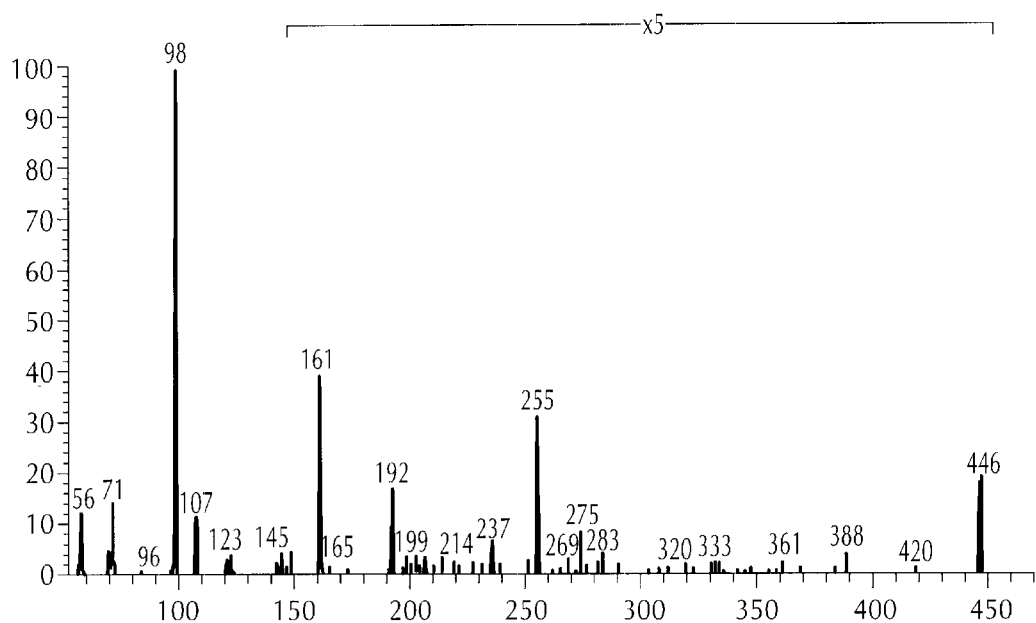
Figure 12A:
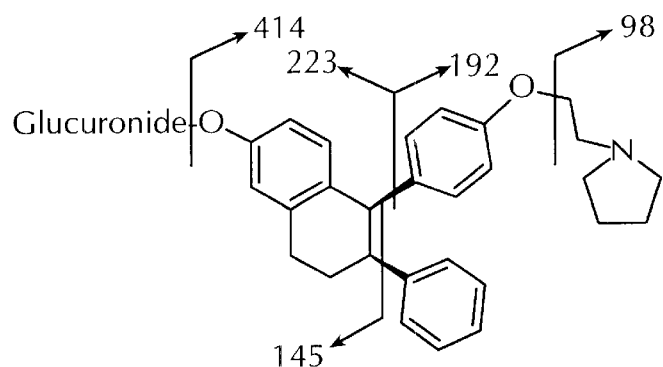
FIG. 12 is the fragmentation pattern and mass spectral data for PPTN metabolite XVII. The scale of the vertical axis is relative abundance. The scale of the horizontal axis is the mass to charge ratio; m/z.
Figure 12B:
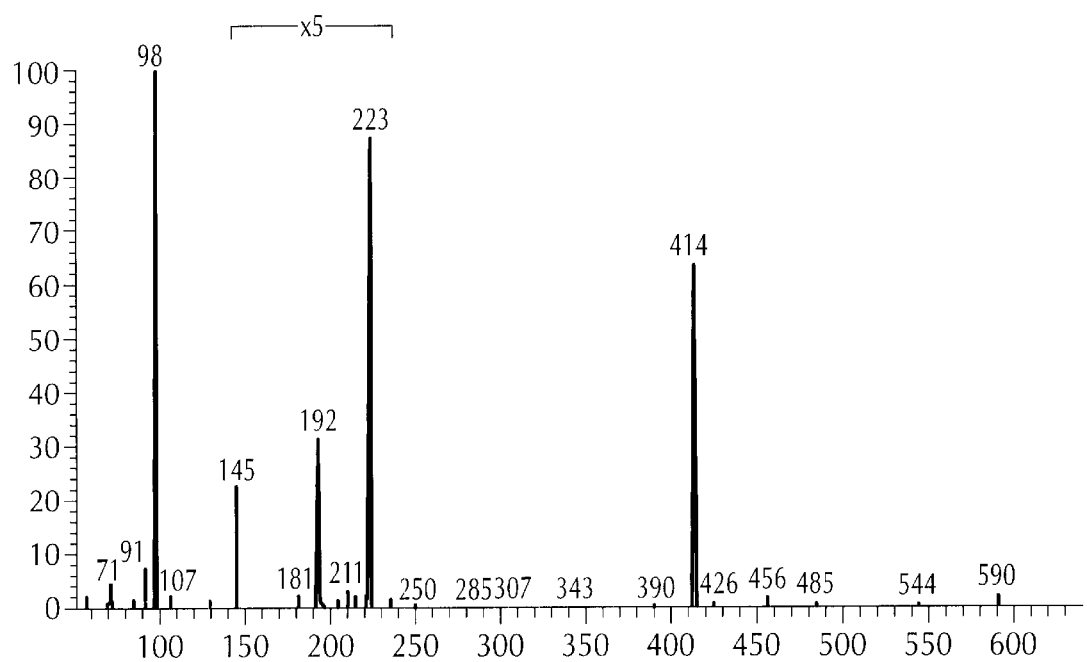
Figure 13A:
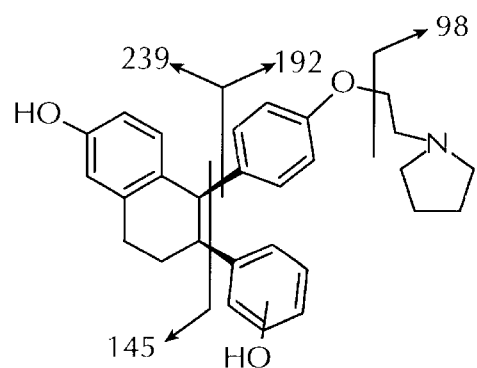
FIG. 13 is the fragmentation pattern and mass spectral data for PPTN metabolite IV. The scale of the vertical axis is relative abundance. The scale of the horizontal axis is the mass to charge ratio; m/z.
Figure 13B:
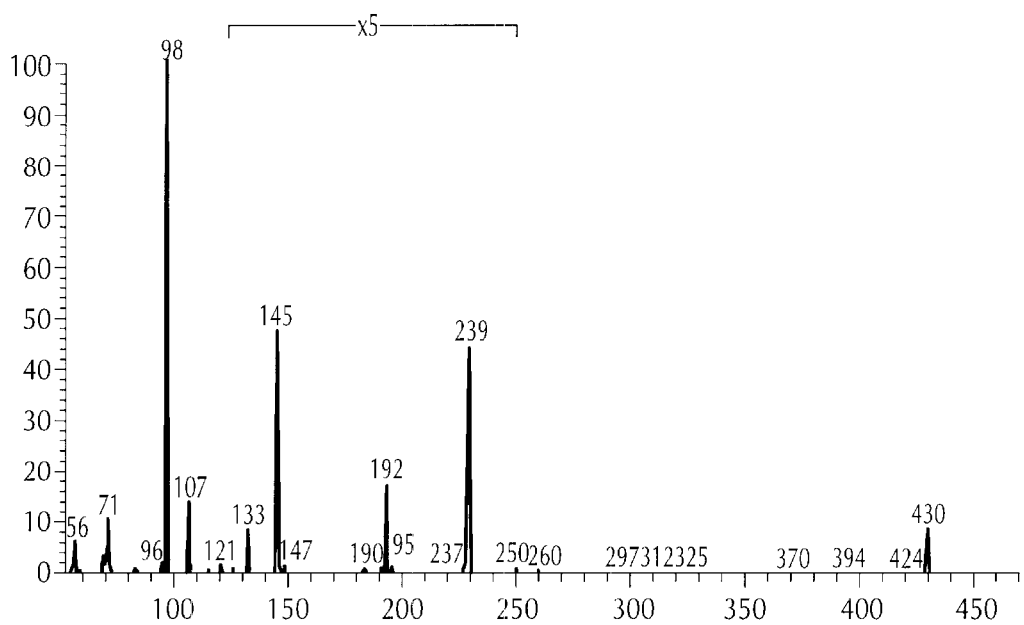
Figure 14A:
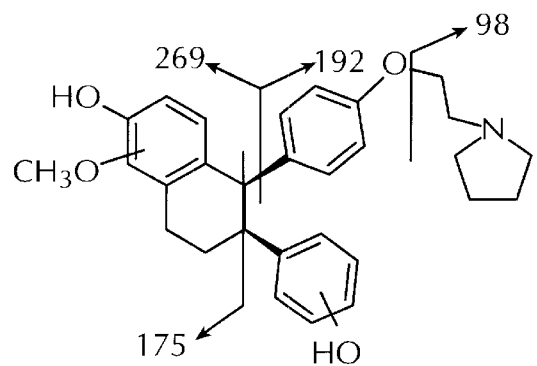
FIG. 14 is the fragmentation pattern and mass spectral data for PPTN metabolite XV. The scale of the vertical axis is relative abundance. The scale of the horizontal axis is the mass to charge ratio; m/z.
Figure 14B:
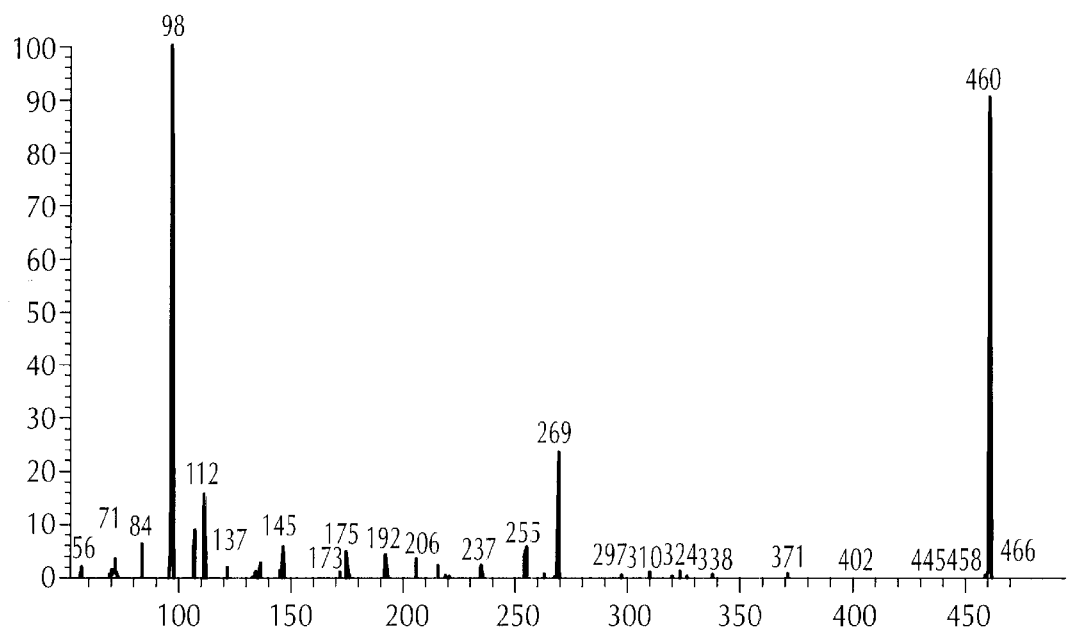
Figure 15A:
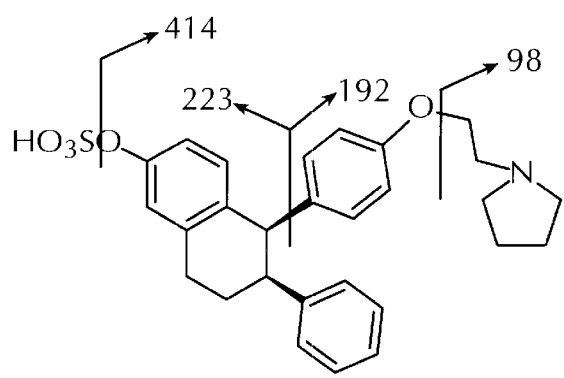
FIG. 15 is the fragmentation pattern and mass spectral data for PPTN metabolite V. The scale of the vertical axis is relative abundance. The scale of the horizontal axis is the mass to charge ratio; m/z.
Figure 15B:
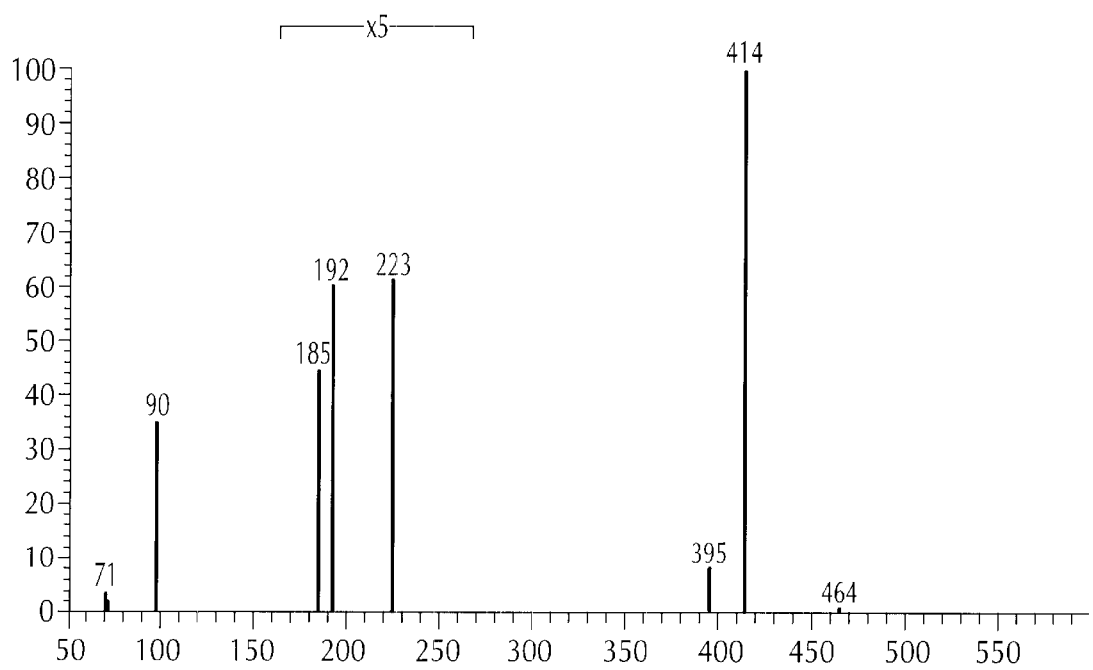
Figure 16A:
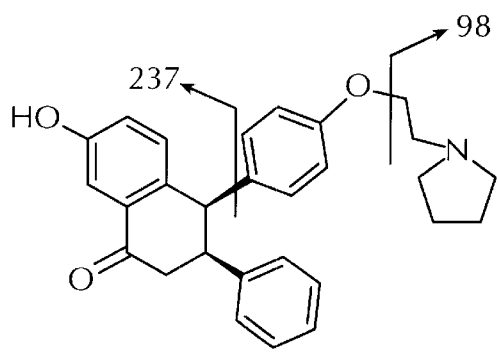
FIG. 16 is the fragmentation pattern and mass spectral data for PPTN metabolite XIII. The scale of the vertical axis is relative abundance. The scale of the horizontal axis is the mass to charge ratio; m/z.
Figure 16B:
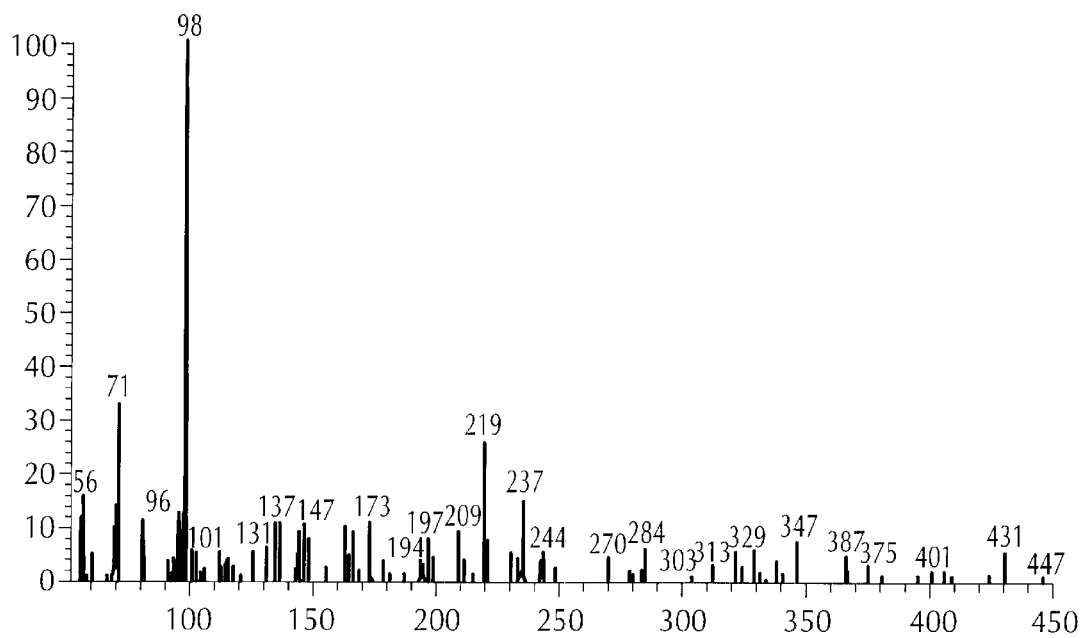
Figure 17A:
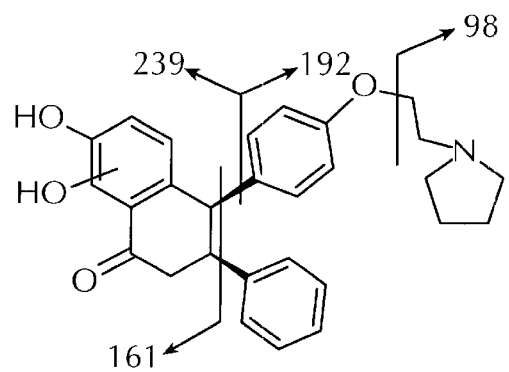
FIG. 17 is the fragmentation pattern and mass spectral data for PPTN metabolite IX. The scale of the vertical axis is relative abundance. The scale of the horizontal axis is the mass to charge ratio; m/z.
Figure 17B:
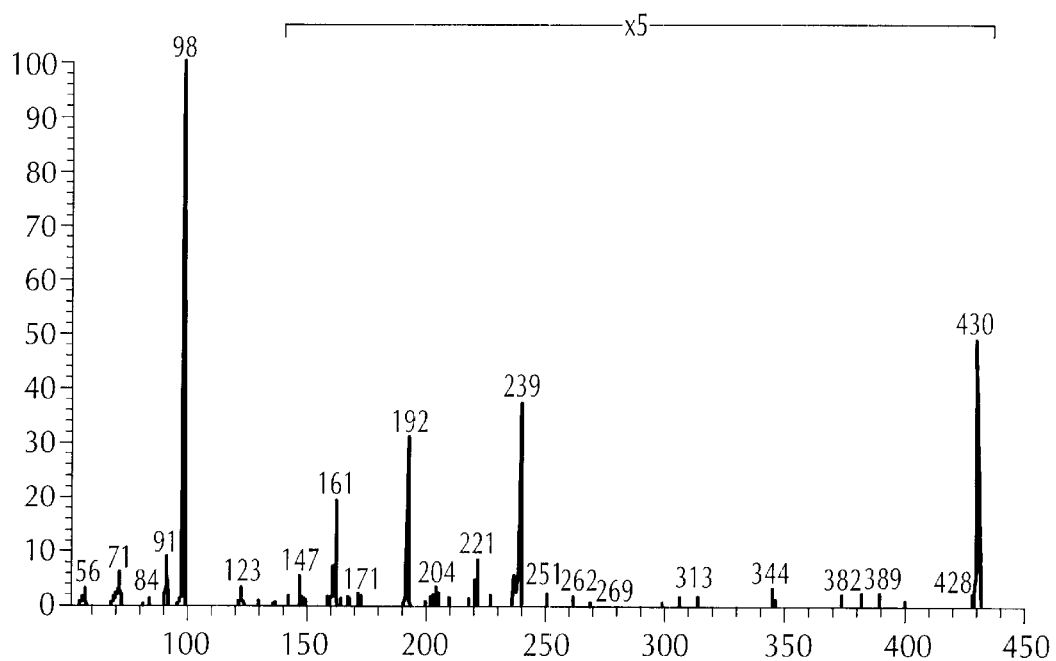
Figure 18A:
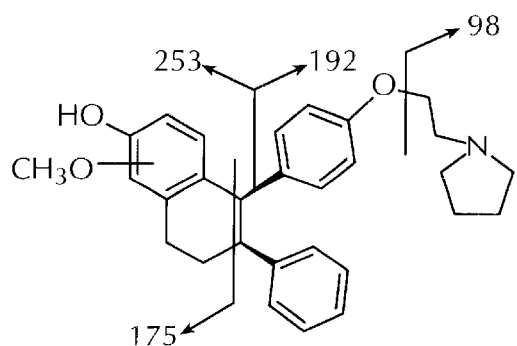
FIG. 18 is the fragmentation pattern and mass spectral data for PPTN metabolite VIII. The scale of the vertical axis is relative abundance. The scale of the horizontal axis is the mass to charge ratio; m/z.
Figure 18B:
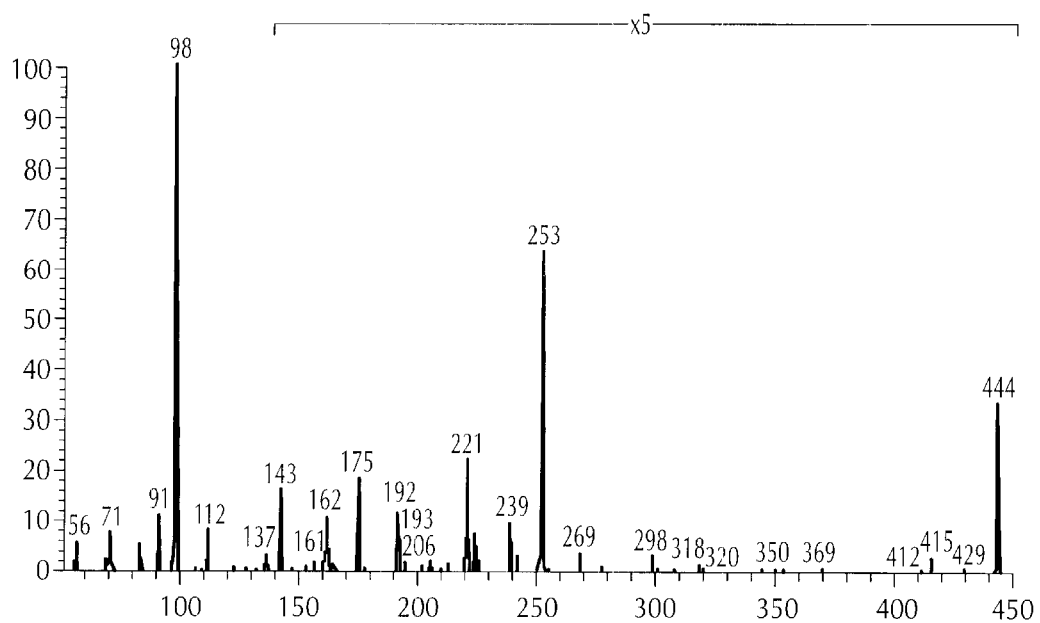

A biosynthesis of PPTN metabolites was carried out in mouse by the methods described in Example 3. Mice were dosed at a dose of 20 mg/kg. Urine and feces were collected from a group of mice. A second group of mice were dosed and blood collected for the isolation and identification of circulating metabolites. The results of the study are presented in FIGS. 1–18. FIGS. 1–3 are representative radiochromatograms of urinary, fecal and circulating metabolites, respectively. Representative mass spectral data together with structural assignments for the metabolites isolated by HPLC are given in FIGS. 4–18.

Scheme 1
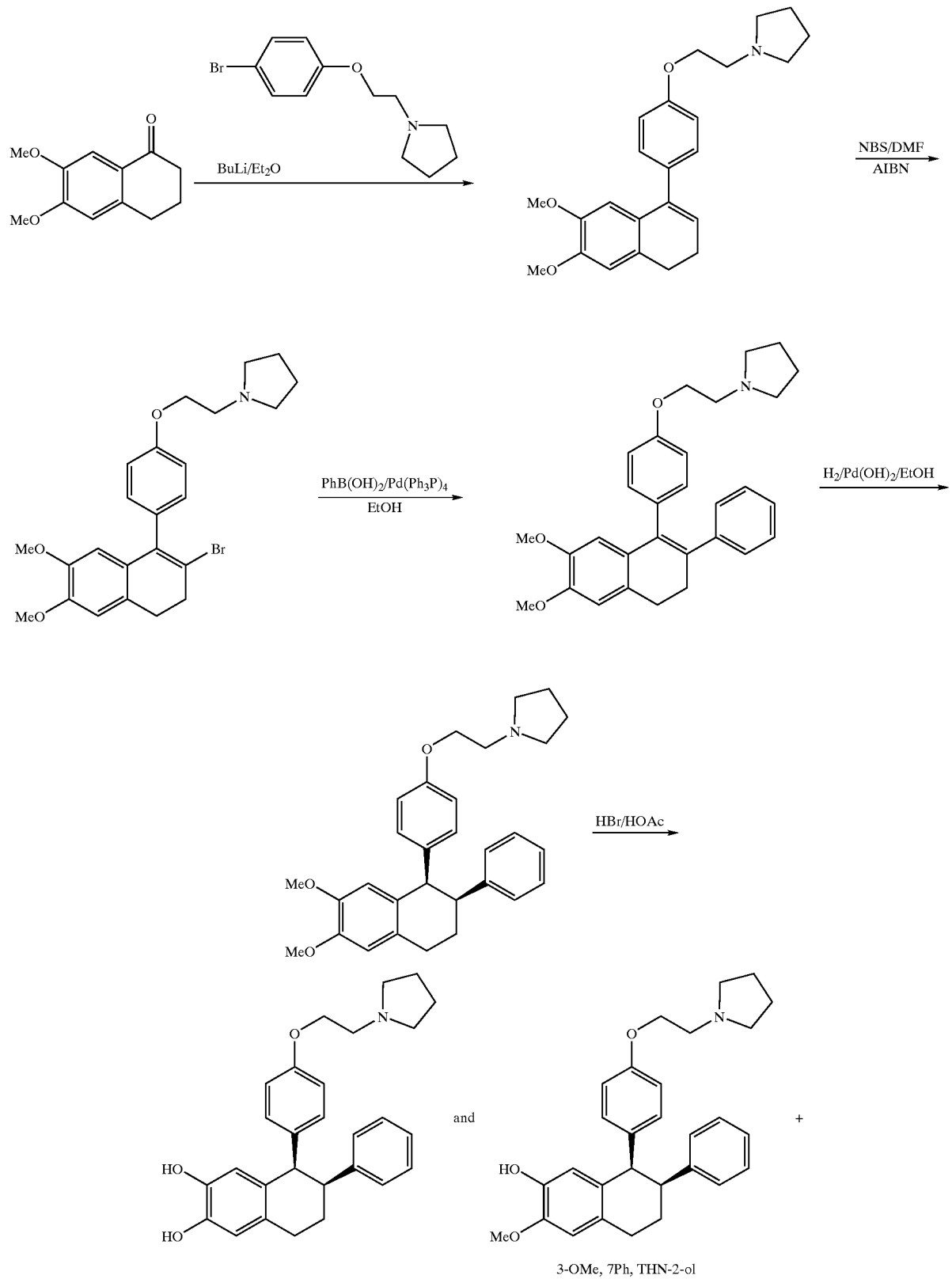

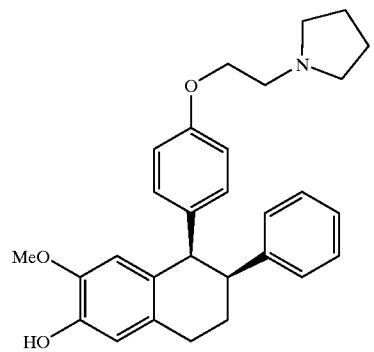

3-OMe, 6Ph, THN-2-ol

Example 1

1-{2-[4-(6,7-Dimethoxy-3,4-dihydro-naphthalen-1-yl)-phenoxy]-ethyl}-pyrrolidine

A solution of 6.75 g (0.025 moles) of 1-(2-(4-bromophenoxy)ethyl)pyrrolidine in 250 ml of ether was cooled to −78° C. under $N_2$. Several ml of THF were added to maintain a clear solution. 16.7 ml of 1.6 M n-butyllithium was added dropwise keeping the temperature below −70° C. After stirring at −78° C. for 1 hour, a solution of 5 g (0.024 moles) of 6,7-dimethoxy-1-tetralone in 25 ml of THF was added dropwise during 1 hour keeping the temperature below −70° C. After stirring for 2.5 hours at −78° C., the reaction was quenched by addition of 100 ml of 2N HCl. The reaction was allowed to warm to room temperature and the pH was adjusted to 7 by addition of 5N NaOH. The $Et_2O$ layer was separated and the aqueous layer was extracted 2 times with EtOAc. The combined $Et_2O$/EtOAc layers were dried over $Na_2SO_4$ and evaporated to give 9 g of crude product, which was purified on 400 g of silica gel eluting with 95/5 $CH_2Cl_2$/MeOH to remove starting tetralone then with 85/15 $CH_2Cl_2$/MeOH to give 3.3 g of product.

NMR ($CDCl_3$) ppm: (1.97, bs, 4H), (2.55, m, 2H), (2.84, t, 2H), (2.98, bs, 4H), (3.19, s, 2H), (3.68, s, 3H), (3.84, s, 3H), (4.31, s, 2H), (5.93, t, 1H), (6.59, s, 1H), (6.73, s, 1H), (6.90, d, 2H), (7.25, d, 2H). Mass spectrum: (parent+1): 379.8.

Starting Materials:
  6,7-dimethoxy-1-tetralone (Aldrich, Milwaukee, Wis.).
  1-[2-(4-bromophenoxy)ethyl]pyrrolidine (Aldrich, Milwaukee, Wis.).

Example 2

1-{2-[4-(2-Bromo-6,7-dimethoxy-3,4-dihydro-naphthalen-1-yl)-phenoxy]-ethyl}-pyrrolidine To a solution of 6 g (0.016 mole) of {2-[4-(6,7-dimethoxy-3,4-dihydronaphthalen-1-yl)-phenoxy]-ethyl}-pyrrolidne in 200 ml of DMF under $N_2$ at room temperature was added dropwise a solution of 2.8 g (0.016 mole) of N-bromosuccinimide in 20 ml of DMF. AIBN (100 mg) was added and the reaction was stirred for 1 hour, then diluted with water and extracted with EtOAc. The EtOAc layer was dried over $Na_2SO_4$ and evaporated to give 7 g of product which was used without purification in the next step.

NMR (acetone-$d_6$) ppm: (1.73, m, 4H), (2.55, m, 4H), (2.80, m, 4H), (3.48, s, 3H), (3.80, s, 3H), (4.15, s, 3H), (6.24, s, 1H), (6.84, s, 1H), (7.00, d, 2H), (7.13, d, 2H). Mass spectrum: (parent+1): 458.

Example 3

1-{2-[4-(6,7-Dimethoxy-2-phenyl-3,4-dihydro-naphthalen-1-yl)-phenoxy]-ethyl}-pyrrolidine A mixture of 7 g (0.015 mole) of 1-{2-[-(2-bromo-6,7-dimethoxy-3,4-dihydro-naphthalen-1-yl)-phenoxy]-ethyl}-pyrrolidine, 5.6 g (0.047 mole) of phenylboronic acid, 620 mg (0.00054 mole) of tetrakis (triphenylphosphine) palladium and 7.6 g (0.072 mole) of sodium carbonate in 500 ml of EtOH was heated under nitrogen for 10 hours. The EtOH was evaporated. Water and EtOAc were added and the EtOAc layer was separated, dried over $Na_2SO_4$ and evaporated to give 9 g of crude product as an oil. The oil was purified on 600 g of silica gel eluting with $CH_2Cl_2$/MeOH 9/1 to give 3.6 g of product.

NMR (acetone $d_6$) ppm: (1.74, m, 4H), (2.60, bs, 2H), (2.71, m, 2H), (2.85, m, 6H), (3.48, s, 3H), (3.82, s, 3H), (4.10, t, 2H), (6.35, s, 1H), (6.80–7.16, m, 10H). Mass Spectrum: (parent+1): 456.

Example 4

1-{2-[4-(6,7-Dimethoxy-2-phenyl-1,2,3,4-tetrahydro-naphthalen-1-yl)-phenoxy]-ethyl}-pyrrolidine A solution of 3.6 g (0.0079 mole) of 1-{2-[4-(6,7-dimethoxy-2-phenyl-3,4-dihydro-naphthalen-1-yl)-phenoxy]-ethyl}-pyrrolidine, 10 ml of 2N HCl, 30 ml $H_2O$ and 100 ml EtOH containing 1.9 g of palladium hydroxide on carbon was shaken in a Parr shaker at 50° C. for 15 hours under a $H_2$ atmosphere of 30 psi (206843 pascal). The reaction was filtered to remove catalyst and the EtOH was evaporated and 5N NaOH was added to adjust the aqueous pH to 8. The aqueous was extracted with EtOAc and the EtOAc layer was dried and evaporated to give 3.0 g of product as a yellow oil.

NMR (acetone $d_6$) ppm: (1.65, m, 4H), (1.74, m, 1 H), (1.90, d, 1H), (2.20, m, 1H), (2.53, bs, 4H), (2.63, t, 2H), (3.00, m, 2H), (2.53, d, 1H), (3.60, s, 3H), (3.80, s, 3H), (3.93, t, 2H), (4.20, d, 1H), (6.35, d, 2H), (6.45, s, 1H), (6.53, d, 2H), (6.68, s, 1H), (7.10, m, 3H). 34 Mass Spectrum: (parent+1): 458.

Example 5

6-Phenyl-5-[4-(2-pyrrolidin-1-yl-ethoxy)-phenyl]-5,6,7,8-tetrahydro-naphthalen-2,3-diol and a mixture of 3-methoxy-7-phenyl-8-[4-(2-pyrrolidin-1-yl-ethoxy)-phenyl]-5,6,7,8-tetrahydronaphthalen-2-ol and 3-methoxy-6-phenyl-5-[4-(2-pyrrolidin-1-yl-ethoxy)-phenyl]-5,6,7,8-tetrahydro-naphthalen-2-ol

A solution of 2 g (0.0044 moles) of 1-{2-[4-(6,7-dimethoxy-2-phenyl-1,2,3,4-tetrahydro-naphthalen-1-yl)-phenoxy]-ethyl}-pyrrolidine, 80 ml of HOAc and 80 ml of 48% aqueous HBr was heated at 90° C. under $N_2$ for 2 hours. The reaction was then cooled to 0° C. in an ice bath. 30% aqueous $NH_4OH$ was added to adjust the pH to 10. The aqueous was extracted with EtOAc and the combined EtOAc layers were dried and evaporated to give 1.6 g of crude products. This material was purified on 120 g silica gel eluting with $CH_2Cl_2$/MeOH 99/1 then 95/5, then 90/10 and finally 85/15 to give 520 mg of a mixture of 3-methoxy-7-phenyl-8-[4-(2-pyrrolidin-1-yl-ethoxy)-phenyl]-5,6,7,8-tetrahydro-naphthalen-2-ol and 3-methoxy-6-phenyl-5-[4-(2-pyrrolidin-1-yl-ethoxy)-phenyl]-5,6,7,8-tetrahydro-naphthalen-2-ol.

NMR (acetone $d_6$) ppm: (1.05, m, 1H), (1.24, d, 1H), (1.76, bs, 5H), (2.20, m, 1H), (3.00, m, 4H), (3.31, d, 1H), (3.82, s, 3H), (4.05, t, 2H), (4.18, d, 1H), (6.34, m, 3H), (6.53, d, 2H), (6.78, s, 1H), (7.85, d, 2H), (7.15, m, 3H), (8.20, bs, 1H). Mass Spectrum: (parent+1): 444.

and then 180 mg of 6-phenyl-5-[4-(2-pyrrolidin-1-yl-ethoxy)-phenyl]-5,6,7,8-tetrahydro-naphthalene-2,3-diol.

NMR (acetone $d_6$): (1.65, m, 4H), (2.20, m, 1H), (2.50, m, 4H), (2,80, m, 4H), (2.95, m, 1H), (3.50, d, 1H), (3.95, t, 2H), (4.05, d, 1H), (6.33, m, 2H), (6.60, d, 2H), (6.66, s, 1H), (6.84, d, 2H), (7.10, m, 3H), (7.55, s, 2H). Mass Spectrum: (parent+1): 430; melting point (mp)-132–134° C.

Scheme 2

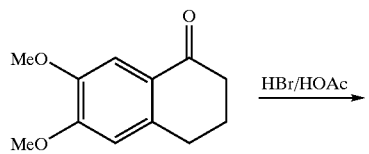

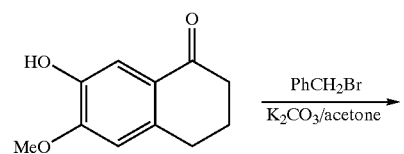

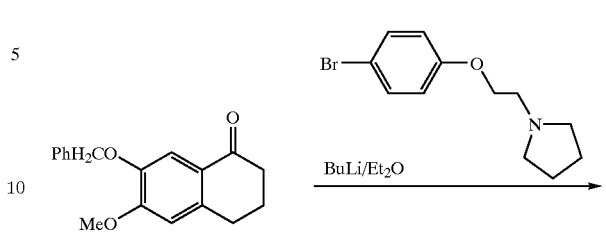

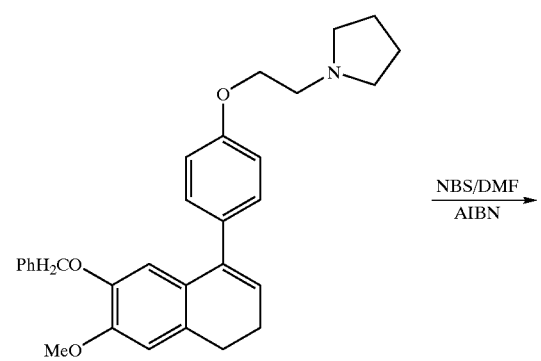

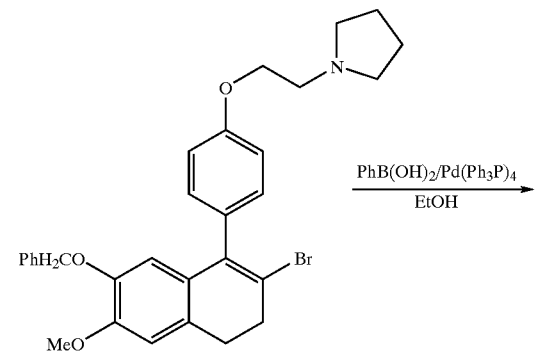

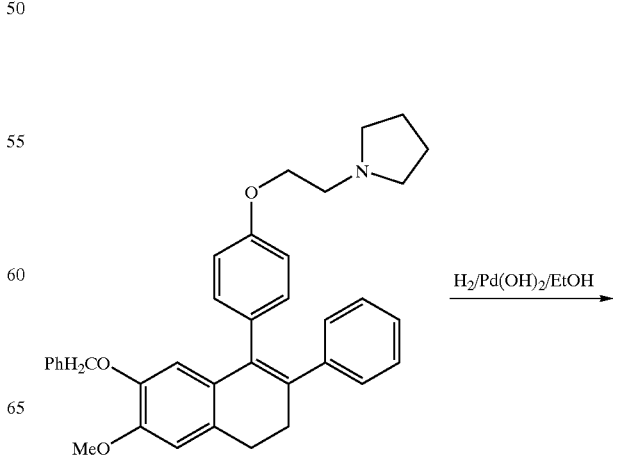

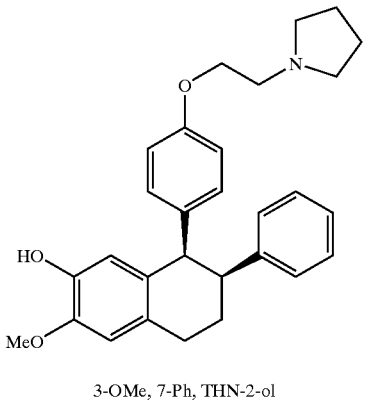

3-OMe, 7-Ph, THN-2-ol

Example 6

7-Hydroxy-6-methoxy-1-tetralone

A solution of 10 g (0.048 mole) of 6,7-dimethoxy-1-tetralone in 100 ml of HOAc and 100 ml of 48% aqueous HBr was heated at 95° C. for 7 hours. The reaction was cooled to room temperature and poured into water and extracted with EtOAc. The EtOAc layer was dried and evaporated to 12 g of crude product. Purification on 1200 g of silica gel eluting with 10% $Et_2O$ in $CH_2Cl_2$ gave 7.5 g of product. Mp 147–148° C. (literature mp 148–152° C., *Journal of Organic Chemistry*, 33, 1968, p. 508).

NMR ($CDCl_3$) ppm: (2.09, m, 2H), (2.58, m, 2H), (2,85, m, 2H), (3.90, s, 3H), (5.50, bs, 1H), (6.64, s, 1H), (7.55, s, 1H). Mass spectrum: (parent+1): 193.
Starting Material: 6,7-dimethoxy-1-tetralone (Aldrich, Milwaukee, Wis.).

Example 7

7-Benzyloxy-6-methoxy-3,4-dihydro-2H-naphthalen-1-one

A mixture of 4.5 g (0.0233 mole) of 7-hydroxy-6-methoxy-1-tetralone, 5.4 g (0.032 mole) of benzyl bromide and 10 g (0.072 mole) of $K_2CO_3$ in 150 ml of acetone was heated to reflux overnight. The reaction as cooled, poured into water and extracted with EtOAc. The EtOAc was dried over $Na_2SO_4$ and evaporated to give 7 g of crude product. Crystallization with $Et_2O$ gave 4.13 g of product as a white solid, mp 110–111° C.

NMR ($CDCl_3$) ppm: (2.09, m, 2H), (2.55, t, 2H), (2.87, t, 2H), (3.90, s, 3H), (5.14, s, 2H), (6.65, s, 1H), (7.25–7.45, m, 5H), (7.58, s, 1H). Mass spectrum: (parent+1): 283.

Example 8

1-{2-[4-(7-Benzyloxy-6-methoxy-3,4-dihydro-naphthalen-1-yl)-phenoxyl]-ethyl}-pyrrolidine Using a procedure analogous to Example 1, from 5.13 g (0.0182 mole) of 7-benzyloxy-6-methoxy-3,4-dihydro-2H-naphthalen-1-one, 13.63 ml of 1.6 M n-butyllithium in hexane, and 5.16 g (0.019 mole) of 1-(2-(4-bromophenoxy) ethyl)pyrrolidine was obtained 3.5 g of the title product.

NMR ($CDCl_3$) ppm: (2.05, bs, 4H), (2.30, m, 2H), (2.74, t, 2H), (3.10–3.40, m, 6H), (3.90, s, 3H), (4.45, bs, 2H), (4.95, s, 2H), (5.90, t, 1H), (6.58, s, 1H),(6.74, s, 1H), (6.80, d, 2H), (7.10, d, 2H), (7.25, m, 5H). Mass Spectrum: (parent+1): 456.

Example 9

1-{2-[4-(7-Benzyloxy-2-bromo-6-methoxy-3,4-dihydro-naphthalen-1-yl)-phenoxy]-ethyl}-pyrrolidine Using a procedure analogous to Example 2, from 2.47 g (0.0054 mole) of 1-{2-[4-(7-benzyloxy-6-methoxy-3,4-dihydro-naphthalen-1-yl)-phenoxy]-ethyl}-pyrrolidine, 965 mg (0.0054 mole) of NBS and 90 mg of AIBN in 50 ml of DMF, was obtained 2.37 g of the title product.

NMR ($CDCl_3$) ppm: (1.90, bs, 4H), (2.69, s, 4H), (2.88, bs, 4H), (3.10, t, 2H), (3.83, t, 2H), (4.83, s, 2H), (6.20, s, 1H), (6.65, s, 1H), (6.90, d, 2H), (7.00, d, 2H), (7.21, m, 5H); Mass spectrum : (parent+1): 536.

Example 10

1-{2-[4-(7-Benzyloxy-6-methoxy-2-phenyl-3,4-dihydro-naphthalen-1-yl)-phenoxy]-ethyl}-pyrrolidine Using a procedure analogous to Example 3, from 2.37 g (0.0044 mole) of 1-{2-[4-(7-benzyloxy-2-bromo-6-methoxy-3,4-dihydro-naphthalen-1-yl)-phenoxy]-ethyl}-pyrrolidine, 1.35 g (0.011 mole) of phenylboronic acid, 153 mg (0.13 mmole) of tetrakis (triphenylphosphine)palladium and 1.88 g (0.017 mole) of $Na_2CO_3$ in 50 ml of EtOH, was obtained 1.38 g of the title product.

NMR ($CDCl_3$) ppm: (1.83, bs, 4H), (2.70, m, 6H), (2.86, m, 2H), (2.96, m, 2H), (3.90, s, 3H), (4.14, t, 2H), (6.37, s, 1H), (6.65–7.30, m, 15H). Mass spectrum: (parent+1): 532.

Example 11

3-Methoxy-7-phenyl-5-[4-(2-pyrrolidin-1-yl-ethoxy)-phenyl]-5,6,7,8-tetrahydro-naphthalen-2-ol A mixture of 1.38 g (0.0026 mole) of 1-{2-[4-(7-Benzyloxy-6-methoxy-2-phenyl-3,4-dihydro-naphthalen-1-yl)-phenoxy]-ethyl}-pyrrolidine, 1.46 g of palladium hydroxide on carbon, 4 ml of 2N HCl, 15 ml of $H_2O$ and 100 ml of EtOH was shaken in a Parr shaker at 50° C. for 36 hrs under a $H_2$ atmosphere of 30 psi. The reaction was filtered to remove catalyst and the EtOH was evaporated. 1N NaOH was added to adjust the ph to 8 and the aqueous was extracted with EtOAc. The EtOAc layer was dried and evaporated to give 640 mg of the title product.

NMR ($CDCl_3$) ppm: (1.80, d, 1H), (1.95, bs, 4H), (2.10, m, 1H), (2.85–3.20, m, 7H), (3.30, d, 1H), (3.88, s, 3H), (4.14, t, 2H), (6.30, d, 2H), (6.43, s, 1H), (6.50, d, 2H), (6.68, s, 1H), (6.80, m, 2H), (7.18, m, 3H); Mass Spectrum: (parent+1): 444.

The 2-OMe, 1-OH metabolite and the 3-OH, 2-OMe metabolite may be synthesized using the procedures outlined in Schemes 4 and 5.

The 3-methoxy-6-phenyl tetrahydro-naphthalen-2-ol metabolite may be synthesized using the procedure outlined in Scheme 5.

Scheme 3
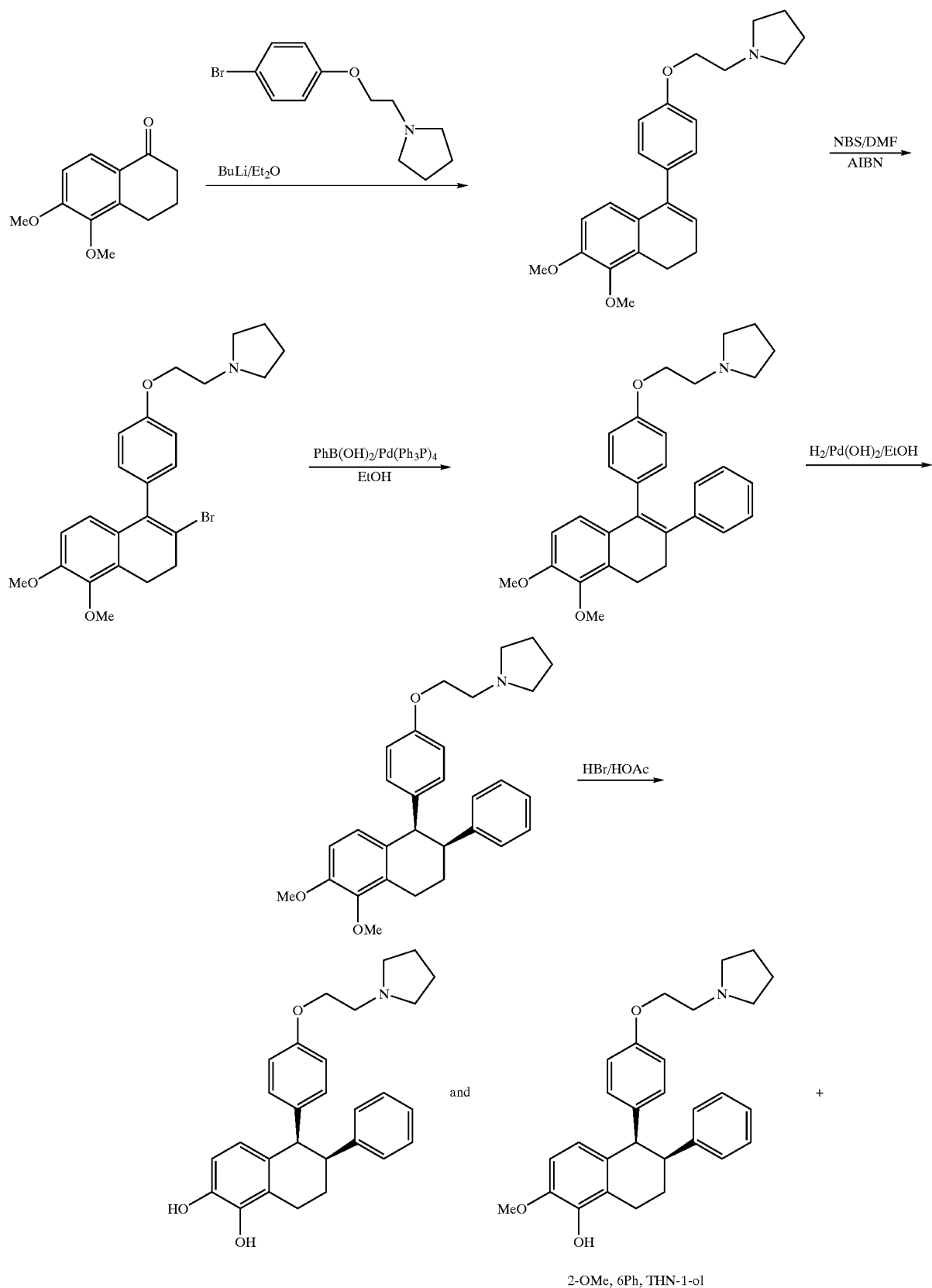
2-OMe, 6Ph, THN-1-ol

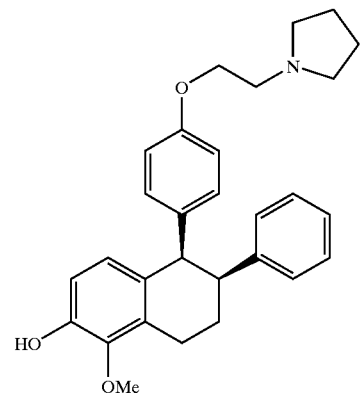

1-OMe, 6Ph, THN-2-ol

Example 12

1-{2-[-4-(5,6-Dimethoxy-3,4-dihydro-naphthalen-1-yl)-phenoxy]-ethyl}-pyrrolidine Using a procedure analogous to Example 1, from 10 g (0.048 mole) of 5,6-dimethoxy-1-tetralone, 33.4 ml of 1.6M n-butyllithium in hexane, and 13.5 g of 1-(2-(4-bromophenoxy)ethyl)pyrrolidine there was obtained 6.5 g of the title product.

NMR (CDCl$_3$) ppm: (1.90, bs, 4H), (2.31, m, 2H), (2.87, t, 2H), (2.90, bs, 4H), (3.10, bs, 2H), (3.78, s, 3H), (3.82, s, 3H), (4.28, bs, 2H), (5.90, s, 1H), (6.63, d, 1H), (6.70, d, 1H), (6.90, d, 2H), (7.22, d, 2H); Mass spectrum: (parent+1): 379.8.

Starting Material 5,6-dimethoxy-1-tetralone; ref: *Organic Process Research & Development*, 1999, 3, 71–72.

Example 13

1-{2-[4-(2-Bromo-5,6-dimethoxy-3,4-dihydro-naphthalen-1-yl)-phenoxy]-ethyl}-pyrrolidne Using a procedure analogous to Example 2, from 5.33 g (0.14 mole) of 1-{2-[4-(5,6-dimethoxy-3,4-dihydro-naphthalen-1-yl)-phenoxy]-ethyl}-pyrrolidine, 2.5 g (0.014 mole) of NBS and 230 mg of AIBN in 50 ml of DMF, there was obtained 6.25 g of the title product.

NMR (CDCl$_3$) ppm: (1.96, bs, 4H), (2.90, m, 6H), (3.05, t, 2H), (3.15, t, 2H), (3.80, s, 6H), (4.30, t, 2H), (6.35, d, 1H), (6.53, d, 1H), (6.95, d, 2H), (7.10, d, 2H); Mass spectrum: (parent+1): 458.

Example 14

1-{2-[4-(5,6-Dimethoxy-2-phenyl-3,4-dihydro-naphthalen-1-yl)-phenoxy]-ethyl}-pyrrolidine Using a procedure analogous to Example 3, from 6.25 g (0.0136 mole) of 1-{2-[4-(2-bromo-5,6-dimethoxy-3,4-dihydro-naphthalen-1-yl)-phenoxy]-ethyl}-pyrrolidine, 4.16 g (0.034 mole) of phenylboronic acid, 472 mg (0.41 mmole) tetrakis (triphenylphospine) palladium and 5.78 g (0.054 mole) of Na$_2$CO$_3$ in 200 ml of EtOH was obtained 6.3 g of the title product.

NMR (CDCl$_3$) ppm: (1.80, bs, 4H), (2.65, bs, 4H), (2.73, t, 2H), (2.90, t, 2H), (3.00, t, 2H), (3.83, s, 6H), (4.08, t, 2H), (6.53, d, 1H), (6.60, d, 1H), (6.74, d, 2H), (6.95, d, 2H), (7.05, m, 5H). Mass Spectrum: (parent+1): 456.

Example 15

1-{2-[4-(5,6-Dimethoxy-2-phenyl-1,2,3,4-tetrahydro-naphthalen-1-yl)-phenoxy]-ethyl}-pyrrolidine Using a procedure analogous to Example 4, from 6.3 g (0.0138 mole) of 1-{2-[4-(5,6-dimethoxy-2-phenyl-3,4-dihydro-naphtlane-1-yl)-phenoxy]-ethyl}-pyrrolidine, 7.7 g (0.055 mole) of palladium hydroxide on carbon, 5 ml of 2NHCl and 10 ml of H$_2$O in 100 ml of EtOH, there was obtained 5.06 g of the title product.

NMR (acetone d$_6$) ppm: (1.95, bs, 4H), (2.70, m, 1H), (2.85, bs, 4H), (2.95, m, 1H), (3.20, bs, 2H), (3.38, bs, 2H), (3.78, s, 3H), (3.82, s, 3H), (4.40, bs, 2H), (6.43, d, 1H), (6.74, d, 1H), (6.85–7.15, m, 7H); Mass Spectrum: (parent+1) :458.

Example 16

6-Phenyl-5-[4-(2-pyrrolidin-1-yl-ethoxy)-phenyl]-5,6,7,8-tetrahydro-naphthalen-1,2-diol and a mixture of 2-methoxy-6-phenyl-5-[4-(2-pyrrolidin-1-yl-ethoxy)-phenyl]-5,6,7,8-tetrahydro-naphthalen-1-ol and 1-methoxy-6-phenyl-5-[4-(2-pyrrolidin-1-yl-ethoxy-phenyl]-5,6,7,8-tetrahydro-naphthalen-2-ol Using a procedure analogous to Example 5, from 2.3 g (0.005 mole) of 1-{2-[4-(5,6-dimethoxy-2-phenyl-1,2,3,4-tetrahydro-naphthalen-1-yl)-phenoxy]-ethyl}-pyrrolidine, 80 ml of HOAc and 80 ml of 48% aqueous HBr, was obtained 650 mg of a mixture of 2-methoxy-6-phenyl-5-[4-(2-pyrrolidin-1-yl-ehtoxy)-phenyl]-5,6,7,8-tetrahydro-naphthalen-1-ol and 1-methoxy-6-phenyl-5-[4-(2-pyrroldin-1-yl-ethoxy)-phenyl]-5,6,7,8-tetrahydro-naphthalen-2-ol.

NMR (CDCl$_3$) ppm: (1.88, bs, 6H), (2.10, m, 1H), (2.84, bs, 4H), (3.00, bs, 2H), (3.25, dt, 1H), (3.35, d, 2H), (3.85, s, 3H), (4.10, bs, 2H), (4.25, d, 1H), (6.25–6.88, m, 8H), (7.15, m, 3H); Mass Spectrum: (parent+1): 444.

and 140 mg of 6-phenyl-5-[4-(2-pyrrolidin-1-yl-ethoxy)-phenyl]-5,6,7,8-tetrahydro-naphthalen-1,2-diol Mass spectrum: (parent+1): 430.

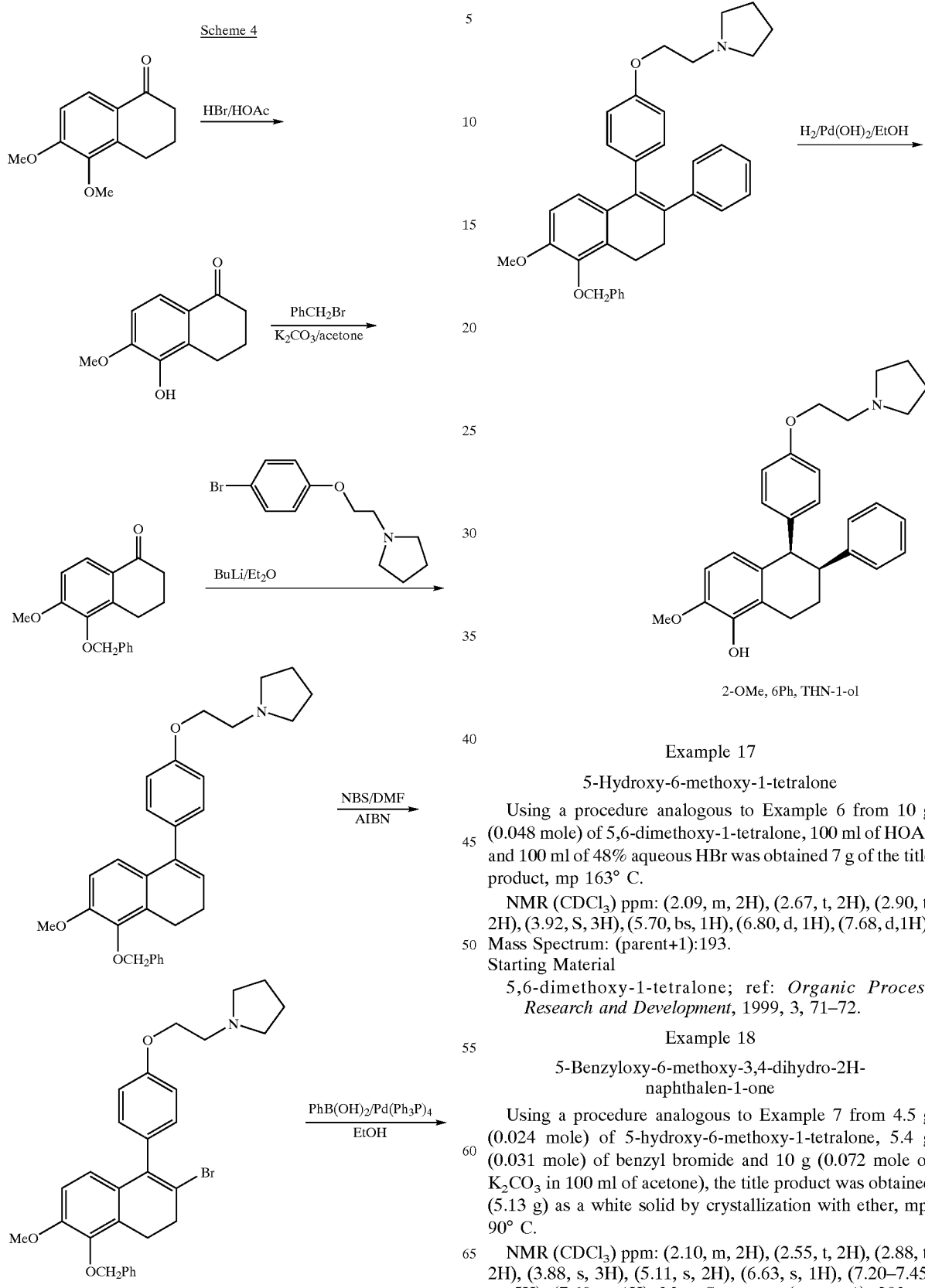

Scheme 4

Example 17

5-Hydroxy-6-methoxy-1-tetralone

Using a procedure analogous to Example 6 from 10 g (0.048 mole) of 5,6-dimethoxy-1-tetralone, 100 ml of HOAc and 100 ml of 48% aqueous HBr was obtained 7 g of the title product, mp 163° C.

NMR (CDCl$_3$) ppm: (2.09, m, 2H), (2.67, t, 2H), (2.90, t, 2H), (3.92, S, 3H), (5.70, bs, 1H), (6.80, d, 1H), (7.68, d,1H). Mass Spectrum: (parent+1):193.
Starting Material
  5,6-dimethoxy-1-tetralone; ref: *Organic Process Research and Development*, 1999, 3, 71–72.

Example 18

5-Benzyloxy-6-methoxy-3,4-dihydro-2H-naphthalen-1-one

Using a procedure analogous to Example 7 from 4.5 g (0.024 mole) of 5-hydroxy-6-methoxy-1-tetralone, 5.4 g (0.031 mole) of benzyl bromide and 10 g (0.072 mole of K$_2$CO$_3$ in 100 ml of acetone), the title product was obtained (5.13 g) as a white solid by crystallization with ether, mp. 90° C.

NMR (CDCl$_3$) ppm: (2.10, m, 2H), (2.55, t, 2H), (2.88, t, 2H), (3.88, s, 3H), (5.11, s, 2H), (6.63, s, 1H), (7.20–7.45, m, 5H), (7.60, s, 1H); Mass Spectrum: (parent+1): 283.

Example 19

1-{2-[4-(5-Benzyloxy-6-methoxy-3,4-dihydro-naphthalen-1-yl)-phenoxy]-ethyl}-pyrrolidine Using a procedure analogous to Example 1, from 10 g (0.3555 mole) of 5-benzyloxy-6-methoxy-3,4-dihydro-2H-naphthalen-1-one, 9.88 g (0.366 mole) of 1-(2-(4-bromophenoxy)ethyl)pyrrolidine and 13.63 ml of 1.6M n-butyllithium in hexane was obtained 4.3 g of the title product.

NMR (CDCl$_3$) ppm: (1.90, bs, 4H), (2.20, m, 2H), (2.78, t, 2H), (2.90, bs, 2H), (3.10, bs, 1H), (3.84, s, 3H), (4.26, t, 2H), (4.98, s, 2H), (5.86, t, 1H), (6.65, d, 1H), (6.74, d, H), (6.88, d, 2H), (7.25, d, 2H), (7.28–7.50, m, 5H).

Example 20

1-{2-[4-(5-Benzyloxy-2-bromo-6-methoxy-3,4-dihydro-naphthalen-1-yl)-phenoxy]-ethyl}-pyrrolidine Using a procedure analogous to Example 2, from 4.3 g (0.0094 mole) of 1-{2-[4-(5-benzyloxy-6-methoxy-3,4-dihydro-naphthalen-1-yl)-phenoxyl]-ethyl}-pyrrolidine, 1.68 g (0.0094 mole) of NBS and 156 mg of AIBN in 50 ml of DMF, there was obtained 4 g of the title product.

NMR (CDCl$_3$) ppm: (1.95, bs, 4H), (2.75, t, 2H), (2.90, t, 2H), (3.00, bs, 4H), (3.10, bs, 2H), (3.80, s, 3H), (4.33, s, 2H), (6.35, d, 1H), (6.57, d, 1H), (6.93, d, 2H), (7.15–7.30, m, 5H); Mass Spectrum: (parent+1): 536.

Example 21

1-{2-[4-(5-Benzyloxy-6-methoxy-2-phenyl-3,4-dihydro-naphthalen-1-yl)-phenoxy]-ethyl}-pyrrolidine Using a procedure analogous to Example 3, from 4.0 g (0.0075 mole) of 1-{2-[4-(5-benzyloxy-2-bromo-6-methoxy-3,4-dihydro-naphthalen-1-yl)-phenoxy]-ethyl}-pyrrolidine, 2.28 g (0.186 mole) of phenylboronic acid, 259 mg (0.224 mmole) of tetrakis(triphenylphospine) palladium, 3.7 g (0.03 mole) of Na$_2$CO$_3$ in 150 ml of EtOH the was obtained 3.2 g of the title product.

NMR (CDCl$_3$) ppm: (1.84, bs, 4H), 2.83, m, 2H), (2.74, m, 4H), (2.95, m, 4H), (3.84, s, 3H), (4.10, t, 2H), (5.03, s, 2H), (6.55, d, 1H), (6.65, d, 1H), (6.75, d, 2H), (6.90–7.50, m, 12H). Mass Spectrum: (parent+1): 532.

Example 22

2-Methoxy-6-phenyl-5-[4-(2-pyrrolidin-1-yl-ethoxy)-phenyl]-5,6,7,8-tetrahydro-naphthalen-1-ol Using a procedure analogous to Example 11, from 3.2 g (0.007 mole) of 1-{2-[4-(5-benzyloxy-6-methoxy-2-phenyl-3,4-dihydronaphthalen-1-yl)-phenoxy]-ethyl)-pyrrolidine, 3.4 g of palladium hydroxide on carbon, 10 ml of 2NHCl, 30 ml of H$_2$O and 100 ml of EtOH, there was obtained 2.2 g of product.

Mass Spectrum: (parent+1): 444.

The 1-methoxy-6-phenyl-tetrahydro-naphthalen-2-ol metabolite can be synthesized as shown in Scheme 6.

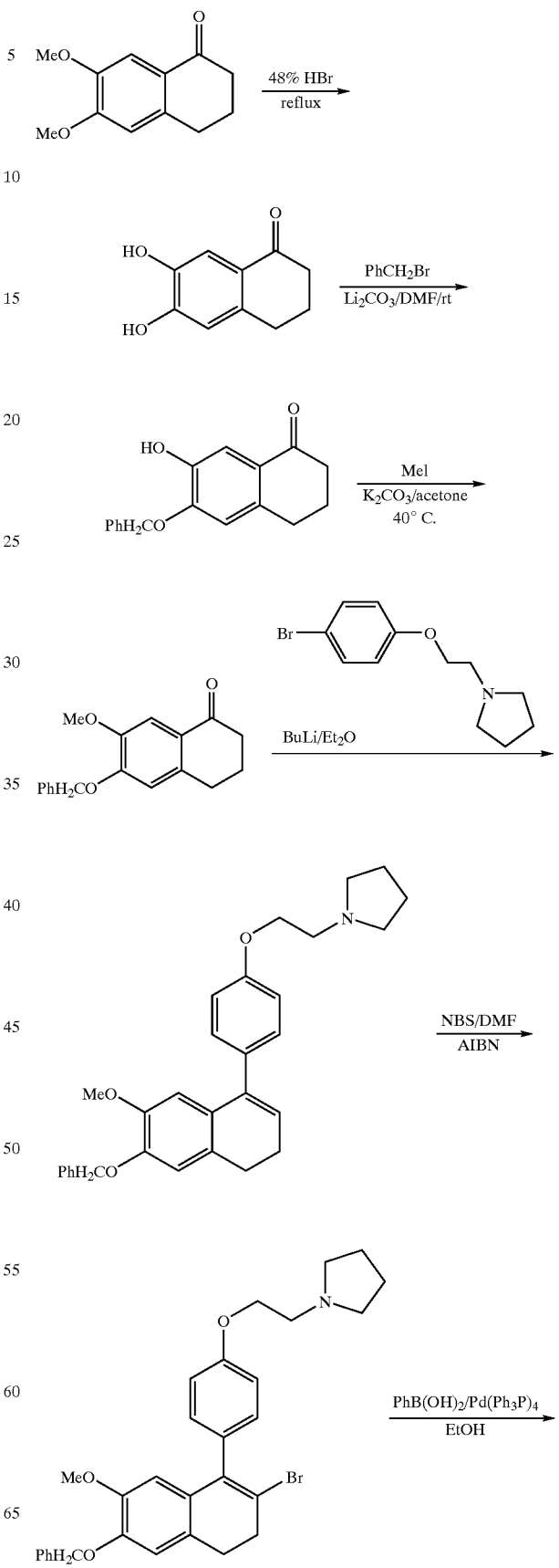

Scheme 5

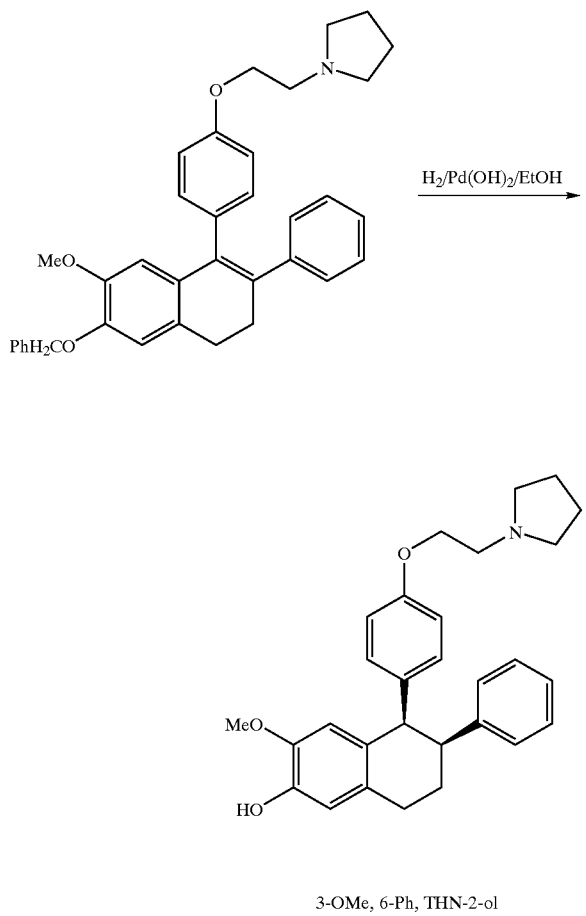
3-OMe, 6-Ph, THN-2-ol
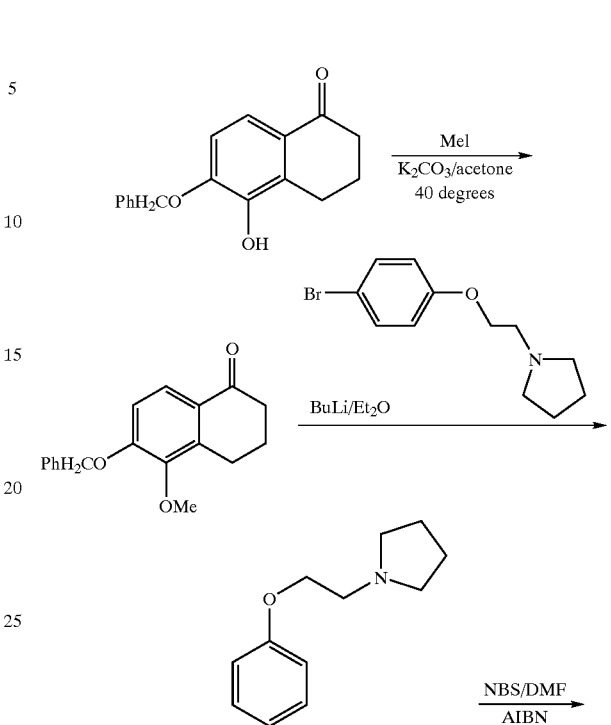
Scheme 6
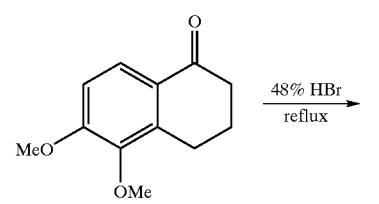
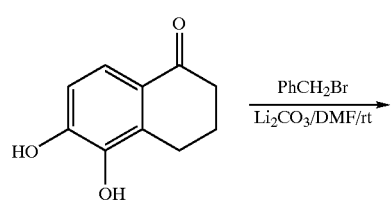
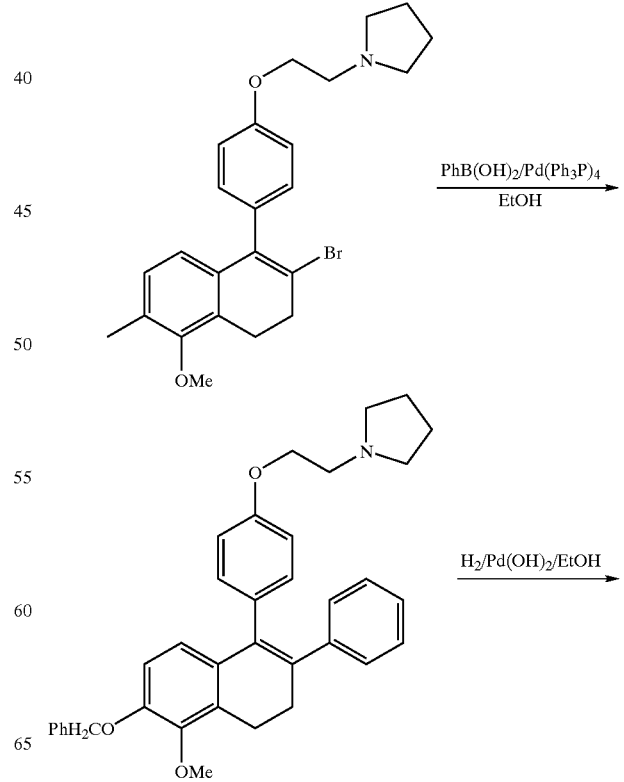

-continued

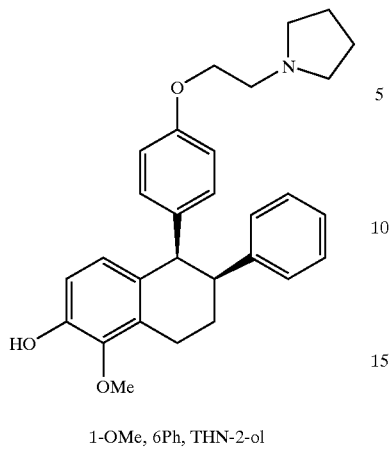

1-OMe, 6Ph, THN-2-ol

What is claimed is:

1. A metabolite of (−)-cis-6-phenyl-5-[4-(2-pyrrolidin-1-yl-ethoxy)-phenyl]-5,6,7,8-tetrahydro-naphthalene-2-ol corresponding to formula I:

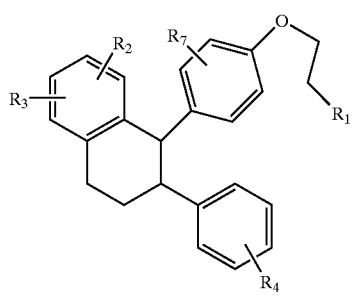
(I)

wherein $R_1$ is selected from

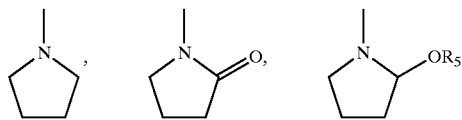

or
NH(CH$_2$)$_3$COR$_6$;
$R_5$ is selected from H or CH$_3$;
$R_2$, $R_3$, $R_4$ and $R_7$ are the same or different and are selected from H and OR$_5$; and
$R_6$ is selected from —OH, or —NHCH$_2$COOH, provided that:
(a) if $R_1$ is

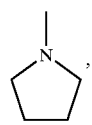

or —NH(CH$_2$)$_3$COOH and
(b) $R_2$ is OH or OCH$_3$ and $R_3$ and $R_7$ are H, or if $R_1$ is as defined in (a) above and
(c) $R_2$ and $R_7$ are H and $R_3$ is OH or OCH$_3$, then $R_4$ is not H;
and further provided that when $R_2$, $R_3$, $R_4$ and $R_7$ are H, then $R_1$ is not

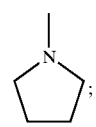

or an optical, stereo, regio or configurational isomer or geometric isomer thereof or a tautomer, pharmaceutically acceptable salt, N-oxide, ester, quaternary ammonium salt, or prodrug thereof.

2. A metabolite of (−)-cis-6-phenyl-5-[4-(2-pyrrolidin-1-yl-ethoxy)-phenyl]-5,6,7,8-tetrahydro-naphthalene-2-ol according to claim 1 that is selected from the group consisting of:

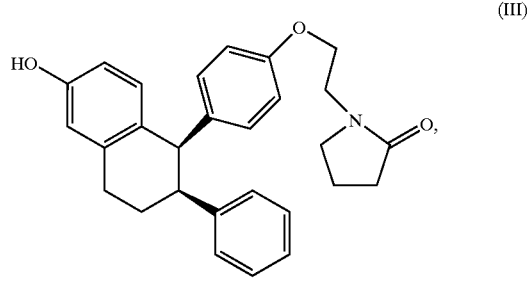
(III)

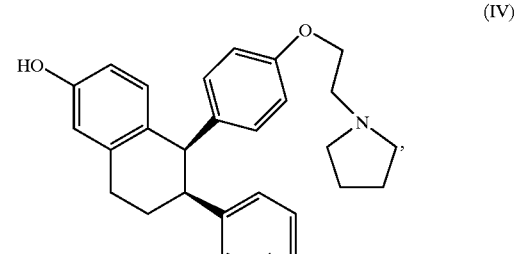
(IV)

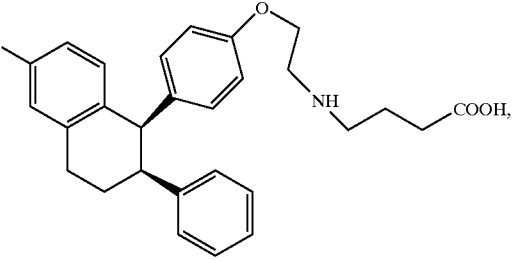
(VII)

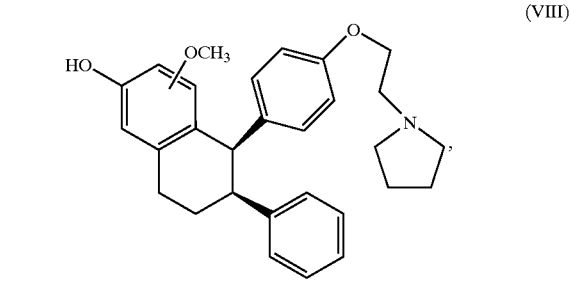
(VIII)

-continued (IX)
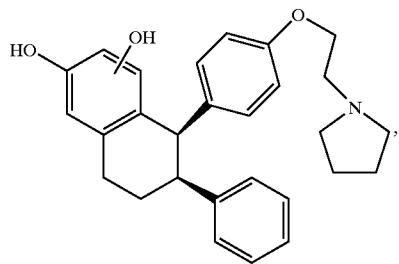

(X)
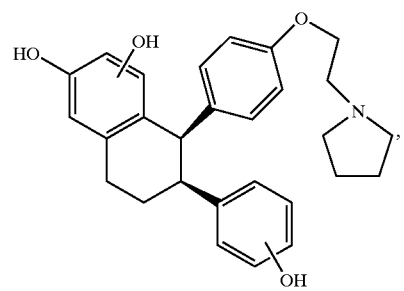

(XIII)
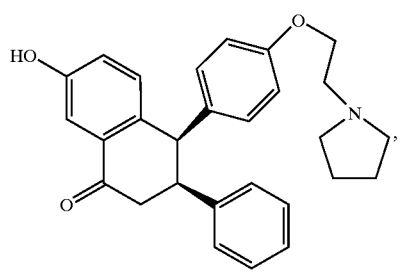

(XV)
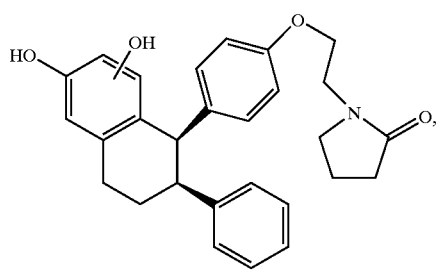

(XIX)

-continued

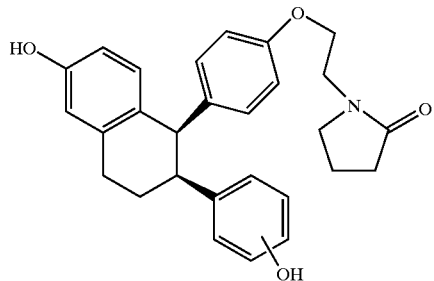
(XXV)

and stereoisomers, tautomers, regio and configurational isomers thereof; and pharmaceutically acceptable salts, N-oxides, esters, quaternary ammonium salts, and prodrugs thereof and combinations thereof.

3. A kit comprising a metabolite of (−)-cis-6-phenyl-5-[4-(2-pyrrolidin-1-yl-ethoxy)-phenyl]-5,6,7,8-tetrahydro-naphthalene-2-ol corresponding to formula I:

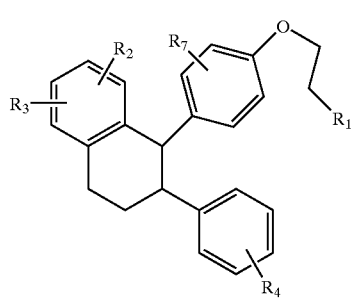
(I)

wherein $R_1$ is selected from

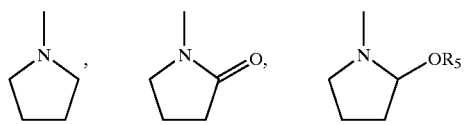

or

—NH(CH$_2$)$_3$COR$_6$;

$R_5$ is selected from H, or CH$_3$;

$R_2$, $R_3$, $R_4$ and $R_7$ are the same or different and are selected from H and OR$_5$; and $R_6$ is selected from —OH, or —NHCH$_2$COOH, provided that:

(a) if $R_1$ is

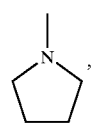

or —NH(CH$_2$)$_3$COOH and (b) R$_2$ is OH or OCH$_3$ and R$_3$ and R$_7$ are H, or if R$_1$ is as defined in (a) above and (c) R$_2$ and R$_7$ are H and R$_3$ is OH or OCH$_3$, then R$_4$ is not H;

and further provided that when R$_2$, R$_3$, R$_4$ and R$_7$ are H, then R$_1$ is not or an optical, stereo, regio or configurational isomer or geometric isomer thereof or a tautomer, pharmaceutically acceptable salt, N-oxide, ester, quaternary ammonium salt, or prodrug thereof.

4. A kit according to claim 3 wherein said metabolite of (−)-cis-6-phenyl-5-[4-(2-pyrrolidin-1-yl-ethoxy)-phenyl]-5,6,7,8-tetrahydro-naphthalene-2-ol is selected from the group consisting of:

-continued (XIX)
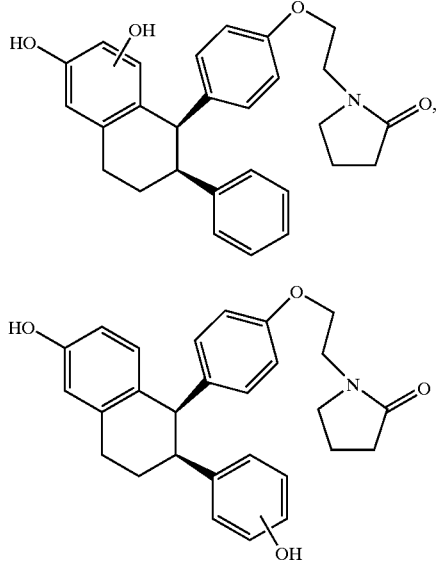

(XXV)
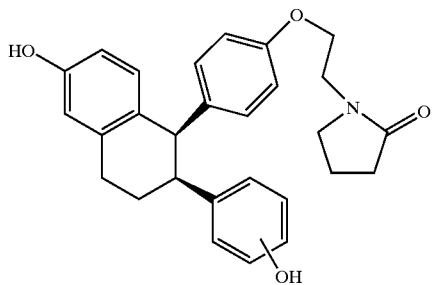

and stereoisomers, tautomers, regio and configurational isomers thereof; and pharmaceutically acceptable salts, N-oxides, esters, quaternary ammonium salts, and prodrugs thereof and combinations thereof.

5. A method of treating disease comprising administering to a subject in need thereof, an effective amount of a metabolite of (−)-cis-6-phenyl-5-[4-(2-pyrrolidin-1-yl-ethoxy)-phenyl]-5,6,7,8-tetrahydro-naphthalene-2-ol corresponding to formula I:

(I)
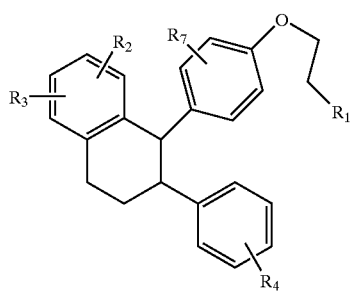

wherein $R_1$ is selected from

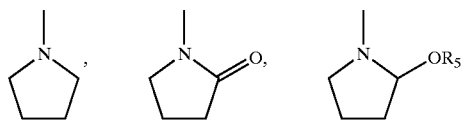

or $NH(CH_2)_3COR_6$;

$R_5$ is selected from H, or $CH_3$;

$R_2$, $R_3$, $R_4$ and $R_7$ are the same or different and are selected from H and $OR_5$; and $R_6$ is selected from —OH, or —NHCH$_2$COOH, provided that:

(a) if $R_1$ is

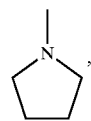

or —NH(CH$_2$)$_3$COOH and (b) $R_2$ is OH or OCH$_3$ and $R_3$ and $R_7$ are H, or if $R_1$ is as defined in (a) above and (c) $R_2$ and $R_7$ are H and $R_3$ is OH or OCH$_3$, then $R_4$ is not H;

and further provided that when $R_2$, $R_3$, $R_4$ and $R_7$ are H, then $R_1$ is not

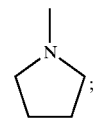

or an optical, stereo, regio or configurational isomer or geometric isomer thereof or a tautomer, pharmaceutically acceptable salt, N-oxide, ester, quaternary ammonium salt, or prodrug thereof.

6. A method as claimed in claim 5 wherein said metabolite of (−)-cis-6-phenyl-5-[4-(2-pyrrolidin-1-yl-ethoxy)-phenyl]-5,6,7,8-tetrahydro-naphthalene-2-ol is selected from the group consisting of:

(III)
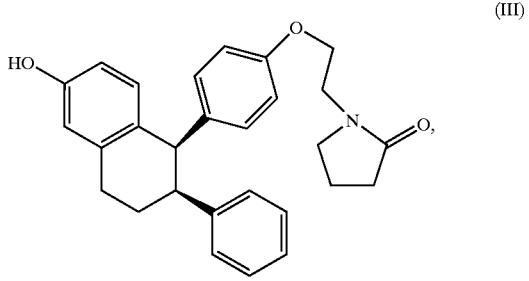

(IV)
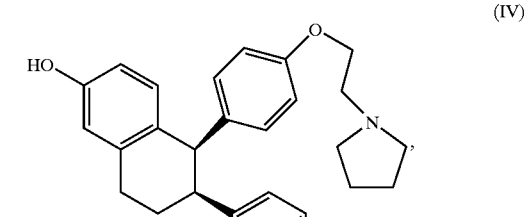

(VII)
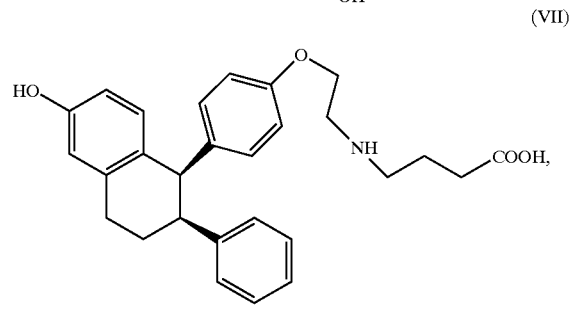

(VIII)
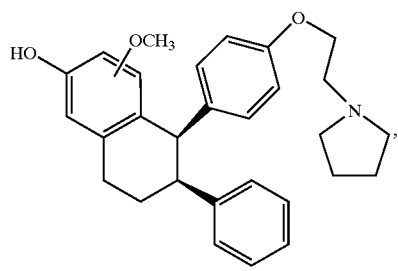

(IX)
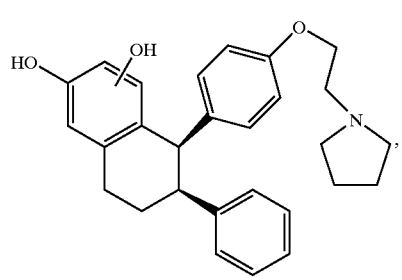

(X)
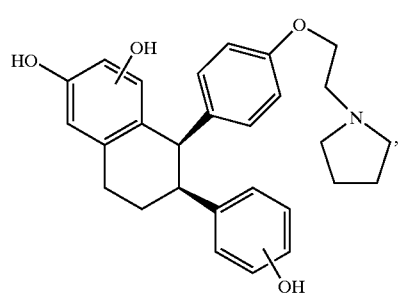

(XIII)
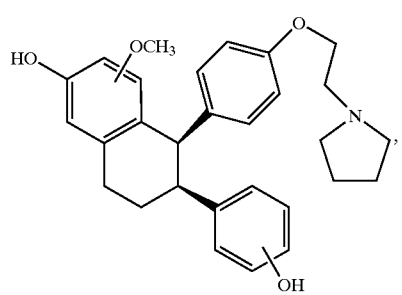

(XV)
(shown below)

(XIX)
(shown at top right)

(XXV)
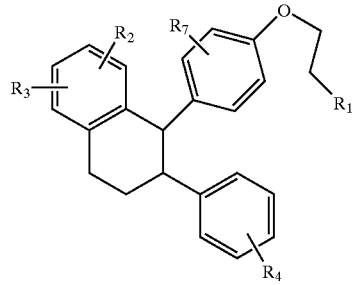

and stereoisomers, tautomers, regio and configurational isomers thereof; and pharmaceutically acceptable salts, N-oxides, esters, quaternary ammonium salts, and prodrugs thereof and combinations thereof.

7. A method as claimed in claim 5 wherein said method substantially reduces the concomitant liability of adverse effects associated with estrogen administration.

8. A method as claimed in claim 6 wherein said method substantially reduces the concomitant liability of adverse effects associated with estrogen administration.

9. A pharmaceutical composition comprising a metabolite of (−)-cis-6-phenyl-5-[4-(2-pyrrolidin-1-yl-ethoxy)-phenyl]-5,6,7,8-tetrahydro-naphthalene-2-ol corresponding to formula I:

(I)

wherein $R_1$ is selected from

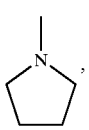 , 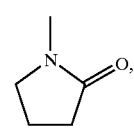 , 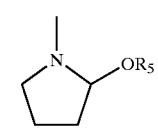

or

—NH(CH$_2$)$_3$COR$_6$;

R$_5$ is selected from H, or CH$_3$;

R$_2$, R$_3$, R$_4$ and R$_7$ are the same or different and are selected from H and OR$_5$; and R$_6$ is selected from —OH, or —NHCH$_2$COOH, provided that:

(a) if R$_1$ is

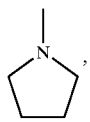

or —NH(CH$_2$)$_3$COOH and (b) R$_2$ is OH or OCH$_3$ and R$_3$ and R$_7$ are H, or if R$_1$ is as defined in (a) above and (c) R$_2$ and R$_7$ are H and R$_3$ is OH or OCH$_3$, then R$_4$ is not H;

and further provided that when R$_2$, R$_3$, R$_4$ and R$_7$ are H, then R$_1$ is not

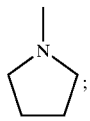

or an optical, stereo, regio or configurational isomer or geometric isomer thereof or a tautomer, pharmaceutically acceptable salt, N-oxide, ester, quaternary ammonium salt, or prodrug thereof, and a pharmaceutically acceptable carrier, vehicle or diluent.

10. A composition according to claim 9 wherein said metabolite of (−)-cis-6-phenyl-5-[4-(2-pyrrolidin-1-yl-ethoxy)-phenyl]-5,6,7,8-tetrahydro-naphthalen-2-ol is selected from the group consisting of:

(III)

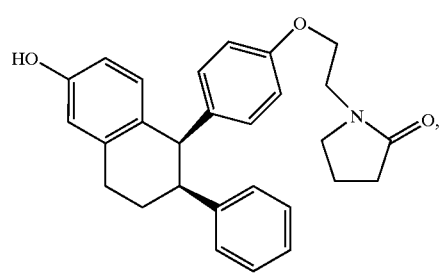

(IV)

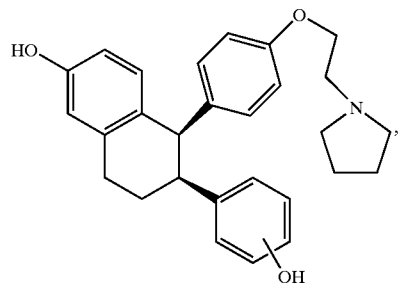

(VII)

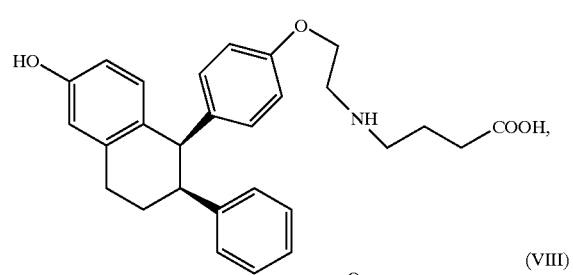

(VIII)

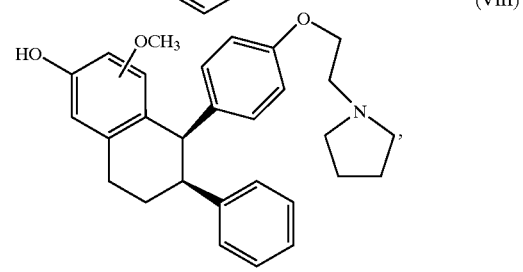

(IX)

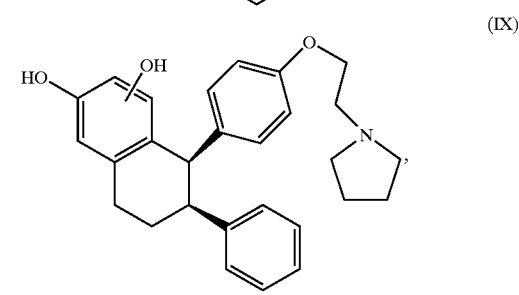

(X)

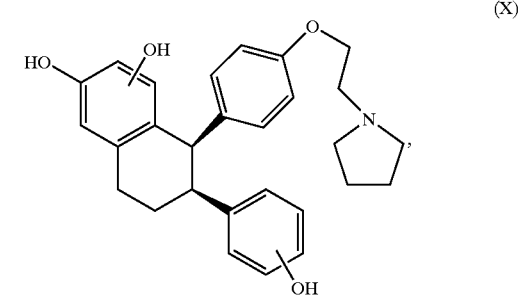

(XIII)

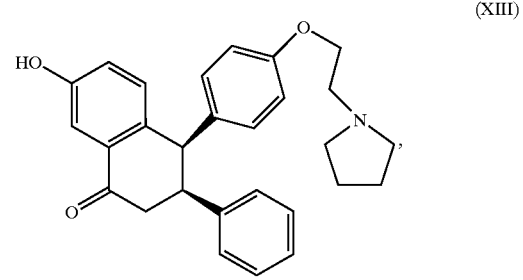

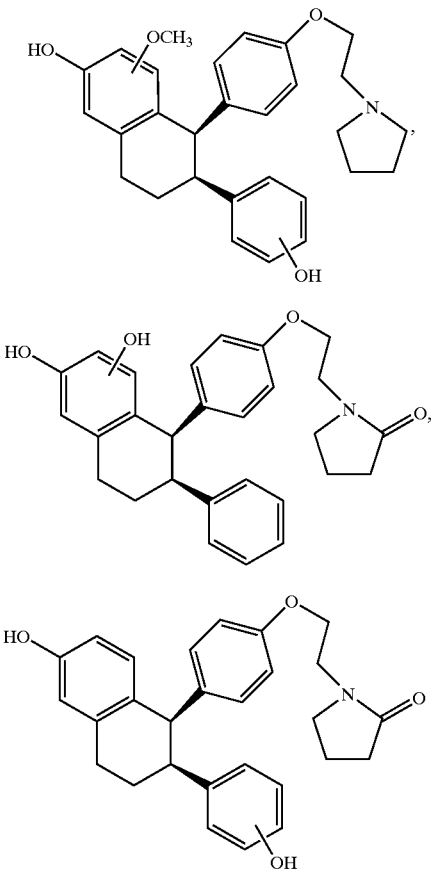

and stereoisomers, tautomers, regio and configurational isomers thereof; and pharmaceutically acceptable salts, N-oxides, esters, quaternary ammonium salts, and prodrugs thereof and combinations thereof.

11. A compound selected from the group consisting of:

6-phenyl-5-[4-(2-pyrrolidin-1-yl-ethoxy)-phenyl]-5,6,7,8-tetrahydro-naphthalen-2,3-diol;

3-methoxy-7-phenyl-8-[4-(2-pyrrolidin-1-yl-ethoxy)-phenyl]-5,6,7,8-tetrahydro-naphthalen-2-ol;

3-methoxy-6-phenyl-5-[4-(2-pyrrolidin-1-yl-ethoxy)-phenyl]-5,6,7,8-tetrahydro-naphthalen-2-ol;

6-phenyl-5-[4-(2-pyrrolidin-1-yl-ethoxy)-phenyl]-5,6,7,8-tetrahydro-naphthalen-1,2-diol;

2-methoxy-6-phenyl-5-[4-(2-pyrrolidin-1-yl-ethoxy)-phenyl]-5,6,7,8-tetrahydro-naphthalen-1-ol;

1-methoxy-6-phenyl-5-[4-(2-pyrrolidin-1-yl-ethoxy-phenyl]-5,6,7,8-tetrahydro-naphthalen-2-ol;

and stereoisomers, tautomers, regio and configurational isomers thereof;

and pharmaceutically acceptable salts, N-oxides, esters, quaternary ammonium salts, and prodrugs thereof and combinations thereof.

* * * * *